(12) United States Patent
Ay et al.

(10) Patent No.: US 11,967,070 B2
(45) Date of Patent: Apr. 23, 2024

(54) SYSTEMS AND METHODS FOR AUTOMATED IMAGE ANALYSIS

(71) Applicant: THE GENERAL HOSPITAL CORPORATION, Boston, MA (US)

(72) Inventors: Hakan Ay, Boston, MA (US); Jayashree Kalpathy-Cramer, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 339 days.

(21) Appl. No.: 17/611,394

(22) PCT Filed: May 13, 2020

(86) PCT No.: PCT/US2020/032678
§ 371 (c)(1),
(2) Date: Nov. 15, 2021

(87) PCT Pub. No.: WO2020/232124
PCT Pub. Date: Nov. 19, 2020

(65) Prior Publication Data
US 2022/0198662 A1    Jun. 23, 2022

Related U.S. Application Data

(60) Provisional application No. 62/847,080, filed on May 13, 2019.

(51) Int. Cl.
*G06T 7/00*    (2017.01)
*A61B 5/00*    (2006.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC ..... G06T 7/0012; G06T 7/11; G06T 2200/04; G06T 2207/10092; G06T 2207/20076;
(Continued)

(56) References Cited

U.S. PATENT DOCUMENTS 9,412,076 B2 *  8/2016  Sapiro ..................... G06F 18/00
9,443,315 B2 *  9/2016  Gall ................. G01R 33/56341
(Continued)

FOREIGN PATENT DOCUMENTS

WO    2019051411 A1    3/2019

OTHER PUBLICATIONS

PCT/US2020/032678—International Search Report and Written Opinion—dated Aug. 12, 2020.

*Primary Examiner* — Neil R McLean
(74) *Attorney, Agent, or Firm* — Quarles & Brady LLP

(57) ABSTRACT

An image analysis system including at least one processor and at least one memory is provided. The image analysis system is configured to receive image data associated with a brain of a patient, the image data including a first three-dimensional (3D) diffusion weighted imaging (DWI) image acquired using a magnetic resonance imaging (MRI) system and a second 3D DWI image, concurrently provide the first 3D DWI image to a first channel of a trained model and the second 3D DWI image to a second channel of the trained model, receive an indicator associated with the first 3D DWI image and the second 3D DWI image from the model, generate a report based on the indicator, and cause the report to be output to at least one of a memory or a display.

23 Claims, 19 Drawing Sheets

(51) Int. Cl.
*A61B 5/055* (2006.01)
*G01R 33/56* (2006.01)
*G01R 33/563* (2006.01)
*G06T 7/11* (2017.01)
*G16H 30/20* (2018.01)

(52) U.S. Cl.
CPC .......... *A61B 5/7267* (2013.01); *A61B 5/7275* (2013.01); *A61B 5/742* (2013.01); *G01R 33/5608* (2013.01); *G01R 33/56341* (2013.01); *G06T 7/11* (2017.01); *G16H 30/20* (2018.01); *A61B 2576/026* (2013.01); *G06T 2200/04* (2013.01); *G06T 2207/10092* (2013.01); *G06T 2207/20076* (2013.01); *G06T 2207/20081* (2013.01); *G06T 2207/20084* (2013.01); *G06T 2207/30016* (2013.01); *G06T 2207/30096* (2013.01)

(58) Field of Classification Search
CPC . G06T 2207/20081; G06T 2207/20084; G06T 2207/30016; G06T 2207/30096; G06T 2207/10081; G06T 2207/10088; G06T 2207/10104; G06T 2207/10136; G06T 2207/20104; A61B 5/0042; A61B 5/055; A61B 5/7267; A61B 5/7275; A61B 5/742; A61B 2576/026; G01R 33/5608; G01R 33/56341; G16H 30/20; G16H 30/40; G16H 50/20; G16H 50/70
USPC ........................................................ 382/131
See application file for complete search history.

(56) References Cited

U.S. PATENT DOCUMENTS

| 2013/0303900 | A1 | 11/2013 | Nowinski | |
|---|---|---|---|---|
| 2018/0137394 | A1 | 5/2018 | Wenzel et al. | |
| 2018/0144467 | A1* | 5/2018 | Sofka | ................... A61B 5/4064 |

* cited by examiner

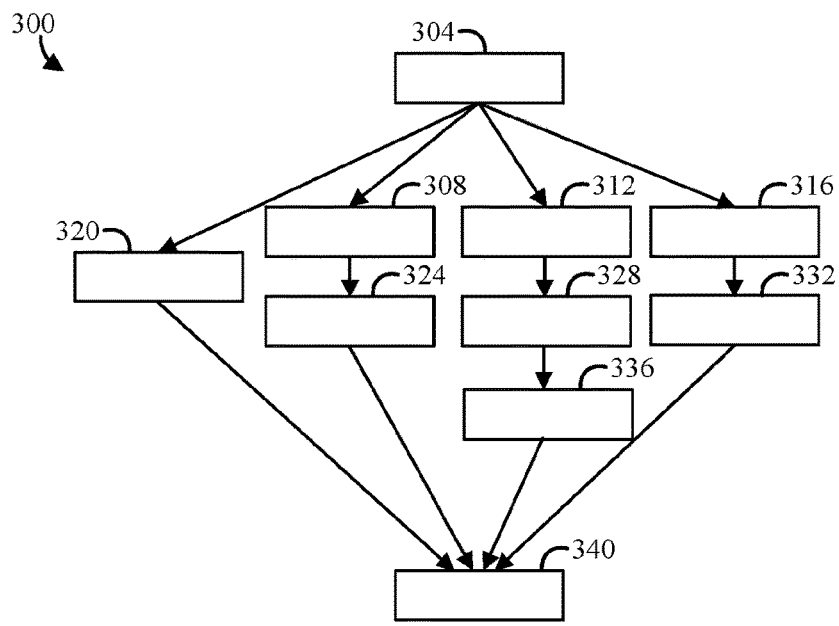
FIG. 3B
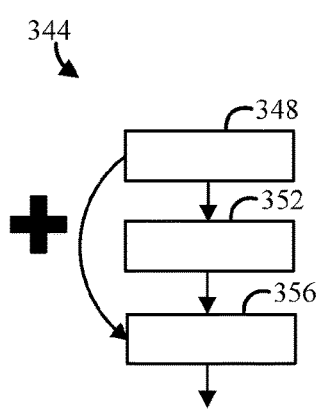
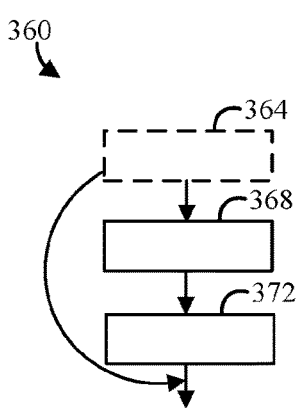
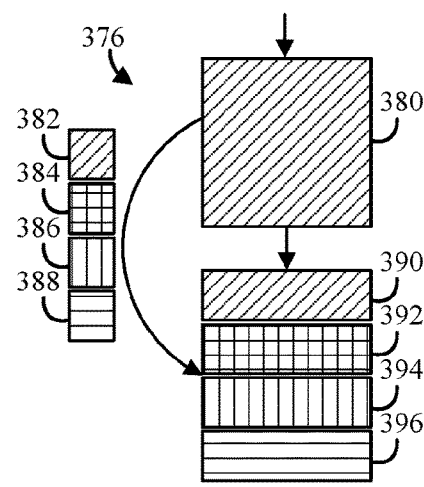
FIG. 3C       FIG. 3D       FIG. 3E FIG. 8A
FIG. 8B

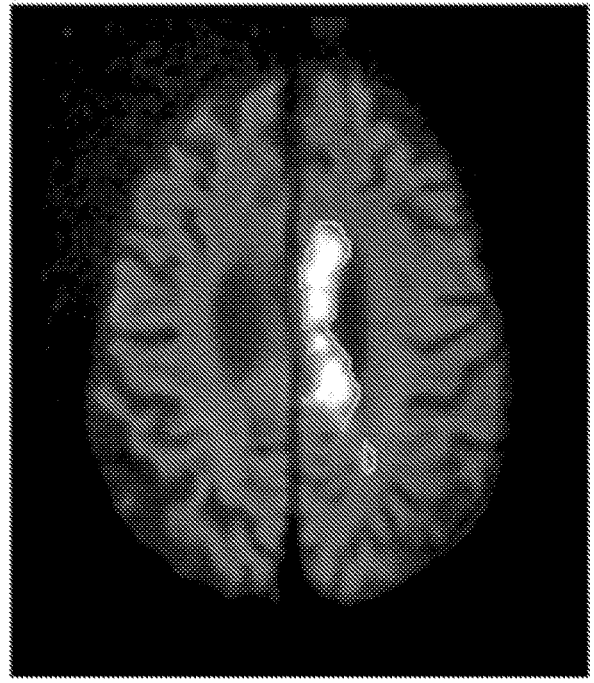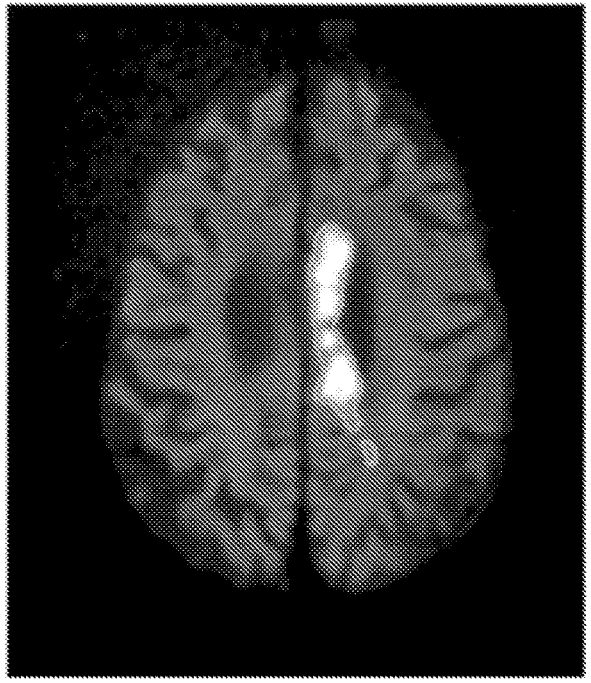
FIG. 8C
FIG. 8D

SYSTEMS AND METHODS FOR AUTOMATED IMAGE ANALYSIS

CROSS REFERENCE TO RELATED APPLICATIONS

This application is a U.S. National Stage of PCT Application No. PCT/US2020/032678 filed on May 13, 2020 which is based on, claims the benefit of, and claims priority to U.S. Provisional Application No. 62/847,080, filed May 13, 2019, which are hereby incorporated by reference herein in their entirety for all purposes.

STATEMENT REGARDING FEDERALLY SPONSORED RESEARCH

This invention was made with government support under 5T32EB1680, R01-NS059710, U01 CA154601, U24 CA180927, U24 CA180918, and P41EB015896 awarded by the National Institutes of Health. The government has certain rights in the invention.

BACKGROUND OF THE INVENTION

Medical imaging is a key tool in the practice of modern clinical medicine. Imaging is used in an extremely broad array of clinical situations, from diagnosis to delivery of therapeutics to guiding surgical procedures. While medical imaging provides an invaluable resource, it also consumes extensive resources. For example, imaging systems are expensive and are efficiently utilized when downtime is controlled. Furthermore, imaging systems require extensive human interaction to setup and operate, and then to analyze the images and make clinical decisions.

As just one example, diffusion weighted imaging (DWI) using magnetic resonance imaging (MRI) is used in stroke evaluation because it allows for assessment of the extent of acute ischemic brain injury. Rapid and accurate evaluation of stroke is imperative as currently available treatments are constrained by a narrow time window. Nonetheless, manual delineation of stroke regions is labor-intensive, time-consuming, and subject to inter-rater variability. Furthermore, ill-defined boundaries as well as variability in size and location of infarcts introduce additional challenge for consistent manual segmentation.

Accurate estimation of the damaged tissue is crucial for assessment for eligibility for intravenous or endovascular reperfusion. In addition, the use of continuous infarct volume data injects statistical power to stroke research. However, segmentation is a highly difficult task as there can be variability in size and location as well as ill-defined boundaries. Certain semi-automatic analysis methods require manual input to detect regions associated with lesions and/or stroke, which can slow analysis and/or introduce variability between human practitioners. Additionally, certain methods of analysis require multiple imaging modalities. Such methods can be susceptible to inaccuracy if there is a defect in acquisition, such as the presence of an imaging artifact. It would therefore be desirable to provide systems and methods that reduce the overall need for human clinicians in medical imaging.

SUMMARY OF THE INVENTION

The present disclosure provides systems and methods that reduce the total investment of human time required for medical imaging applications. In one non-limiting example, systems and methods are provided for automatically analyzing images, for example, such as diffusion weighted magnetic resonance imaging (DWI).

In accordance with one aspect of the disclosure, an image analysis system including at least one processor and at least one memory is provided. The image analysis system is configured to receive image data associated with a brain of a patient, the image data including a first three-dimensional (3D) diffusion weighted imaging (DWI) image acquired using a magnetic resonance imaging (MRI) system and a second 3D DWI image, concurrently provide the first 3D DWI image to a first channel of a trained model and the second 3D DWI image to a second channel of the trained model, receive an indicator associated with the first 3D DWI image and the second 3D DWI image from the model, generate a report based on the indicator, and cause the report to be output to at least one of a memory or a display.

In accordance with another aspect of the disclosure, an image analysis method is provided. The image analysis method includes receiving image data associated with a brain of a patient, the image data including a first three-dimensional (3D) diffusion weighted image (DWI) image acquired using a magnetic resonance imaging (MRI) system and a second 3D DWI image, concurrently providing the first 3D DWI image to a first channel of a trained model and the second 3D DWI image to a second channel of the trained model, receiving an indicator associated with the first 3D DWI image and the second 3D DWI image from the model, generating a report based on the indicator, and causing the report to be output to at least one of a memory or a display.

In accordance with yet another aspect of the disclosure, an ischemic stroke analysis system including at least one processor and at least one memory is provided. The ischemic stroke analysis system is configured to receive image data associated with a brain of a patient, the image data including a first three-dimensional (3D) diffusion weighted imaging (DWI) image and a second 3D DWI image acquired using a magnetic resonance imaging (MRI) system, provide the image data to a trained model, receive an indicator associated with the first 3D DWI image and the second 3D DWI image from the model, generate a report comprising a segmentation map of lesions in the brain of the patient based on the indicator, and cause the report to be output to at least one of a memory or a display.

The foregoing and other aspects and advantages of the invention will appear from the following description. In the description, reference is made to the accompanying drawings which form a part hereof, and in which there is shown by way of illustration embodiments of the invention. Any such embodiment does not necessarily represent the full scope of the invention, however, and reference is made therefore to the claims and herein for interpreting the scope of the invention.

BRIEF DESCRIPTION OF THE DRAWINGS

FIG. 3B is an example of an inception module for use with the model in FIG. 3A.

FIG. 3C is an example of a residual connection.

FIG. 3D is an example of a dense connection.

FIG. 3E is an example of a squeeze-and-excitation module.

FIG. 8A is an example of a manual segmentation on a first DWI image.

FIG. 8B is an example of a model generated segmentation on the first DWI image.

FIG. 8C is an example of a manual segmentation on a second DWI image.

FIG. 8D is an example of a model generated segmentation on the second DWI image.

DETAILED DESCRIPTION OF THE INVENTION

The present disclosure provides systems and methods that can reduce human and/or trained clinician time required to analyze medical images. As one non-limiting example, the present disclosure provides example of the inventive concepts provided herein applied to the analysis of diffusion weighted magnetic resonance imaging, however, other imaging modalities beyond MRI and applications within each modality are contemplated, such as ultrasound, computed tomography (CT), positron emission tomography (PET), optical, digital pathological imaging, and the like.

In the non-limiting example of DWI images, the systems and methods provided herein can determine ischemic stroke areas in a patient brain using an input DWI image of the patient brain.

Figure 1:
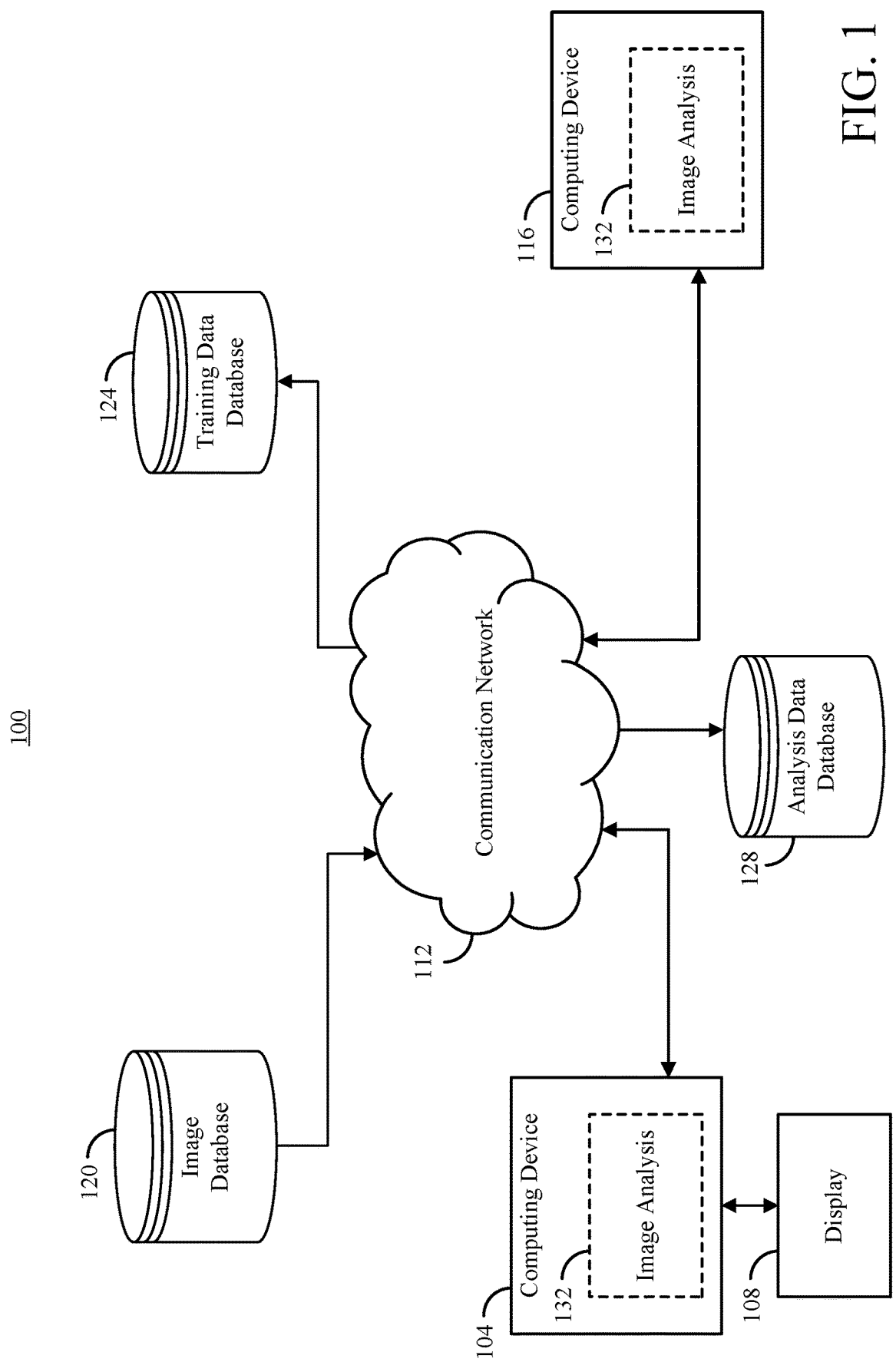
FIG. 1 is an example of an image analysis system in accordance with the disclosed subject matter.

FIG. 1 shows an example of an image analysis system 100 in accordance with some aspects of the disclosed subject matter. In some configurations, the image analysis system 100 can include a computing device 104, a display 108, a communication network 112, a supplemental computing device 116, an image database 120, a training data database 124, and an analysis data database 128. In this way the image analysis system 100 can be referred to as an image analysis system 100. The computing device 104 can be in communication (e.g., wired communication, wireless communication) with the display 108, the supplemental computing device 116, the image database 120, the training data database 124, and the analysis data database 128.

The computing device 104 can implement portions of an image analysis application 132, which can involve the computing device 104 transmitting and/or receiving instructions, data, commands, etc. from one or more other devices. For example, the computing device 104 can receive image data from the image database 120, receive training data from the training data database 124, and/or transmit reports and/or raw data generated by the image analysis application 132 to the display 108 and/or the analysis data database 128.

The supplementary computing device 116 can implement portions of the image analysis application 132. It is understood that the image analysis system 100 can implement the image analysis application 132 without the supplemental computing device 116. In some aspects, the computing device 104 can cause the supplemental computing device 116 to receive image data from the image database 120, receive training data from the training data database 124, and/or transmit reports and/or raw data generated by the image analysis application 132 to the display 108 and/or the analysis data database 128. In this way, a majority of the image analysis application 132 can be implemented by the supplementary computing device 116, which can allow a larger range of device to be used as the computing device 104 because the required processing power of the computing device 104 may be reduced.

The image database 120 can include image data. In one non-limiting example, the images may include images of a brain of a patient. In some aspects, the brain images can be or include a DWI images. The image data can include a number of DWI images associated with a patient. In some aspects, multiple DWI images can be associated with a single patient. For example, a first DWI image and a second DWI image can be associated with a target patient. In some aspects, the first DWI image and the second DWI image can be generated using different imaging parameters. For example, the first DWI image can be generated using a b value of zero, and the second DWI image can be generated using a b value of one thousand. The b value may also be referred to as a "b factor." In some aspects, the image database 120 can also include attributes about a patient associated with an image and/or image metadata. In some aspects, the image metadata can include information about how the image was generated (e.g., b value), what system was used to generate the image (e.g., a 1.5T General Electric magnetic resonance (MR) instrument and/or a 1.5T Siemens MR instrument), the date the image was generated, a medical facility (e.g., a hospital) that generated the image, image scaling data, etc.

The training data database 124 can include training data that the image analysis application 132 can use to train one or more machine learning models including networks such as convolutional neural networks (CNNs). More specifically, the training data can include annotated training images (e.g., human annotated training images) that can be used to train one or more machine learning models using a supervised learning process. The training data will be discussed in further detail below.

The image analysis application 132 can automatically generate one or more metrics related to stroke (e.g., ischemic stroke) based on an image. For example, the image analysis application 132 can automatically generate an indication of a stroke occurrence, a volume of one or more lesions, a location of one or more lesions, and/or other stroke metrics. The image analysis application 132 can also automatically generate one or more reports based on indication of a stroke occurrence, a volume of one or more lesions, a location of one or more lesions, and/or other stroke metrics (and by extension, the image). The image analysis application 132 can output one or more of the stroke metrics and/or reports to the display 108 (e.g., in order to display the stroke metrics and/or reports to a medical practitioner) and/or to a memory, such as a memory included in the analysis data database 128 (e.g., in order to store the metrics and/or reports).

As shown in FIG. 1, the communication network 112 can facilitate communication between the computing device 104, the supplemental computing device 116, the image database 120, the training data database 124, and the analysis data database 128. In some configurations, the communication network 112 can be any suitable communication network or combination of communication networks. For example, the communication network 112 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some configurations, the communication network 112 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, and the like.

Figure 2:
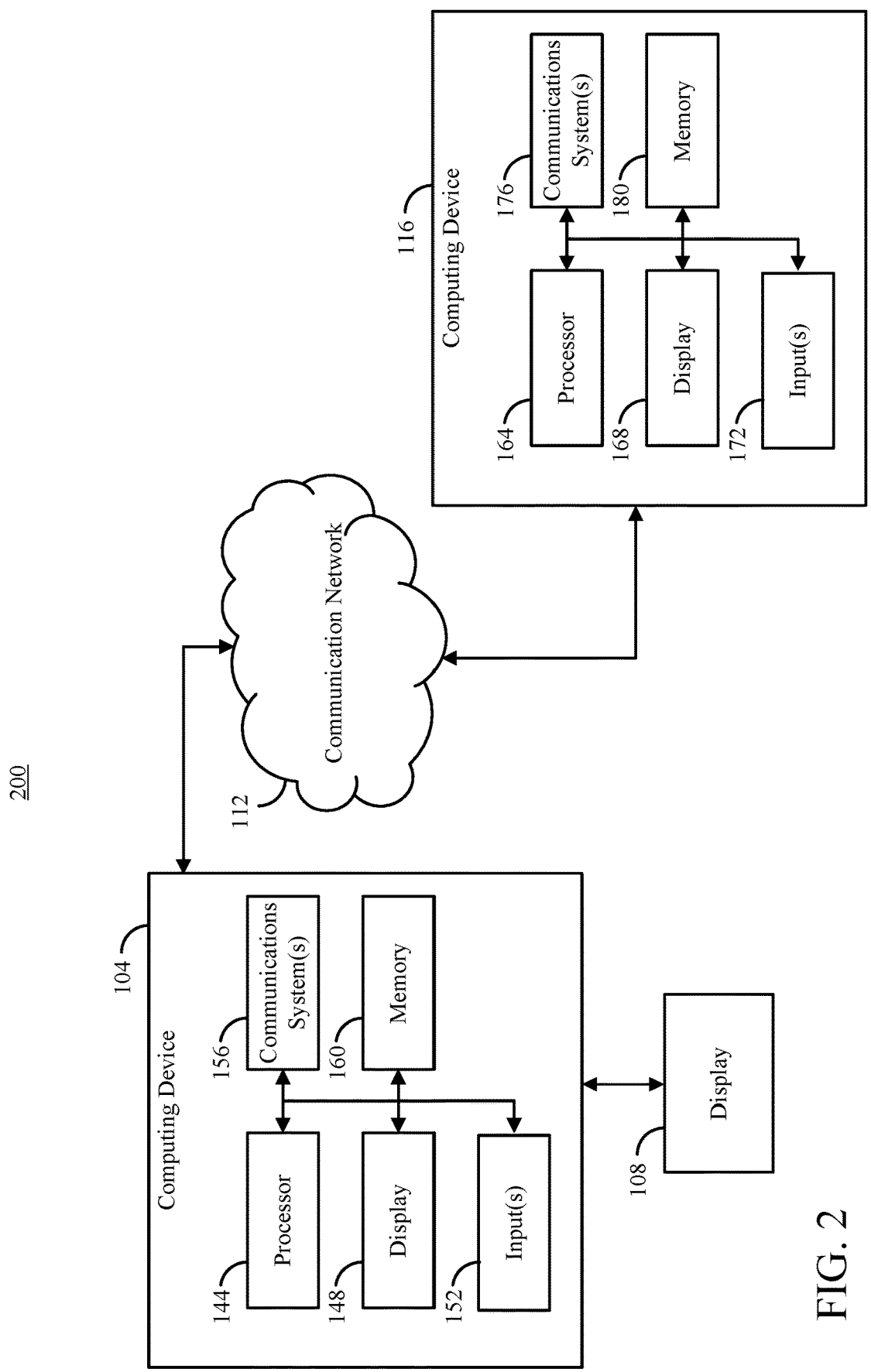
FIG. 2 is an example of hardware that can be used to implement a computing device and a supplemental computing device shown in FIG. 1 in accordance with the disclosed subject matter.

FIG. 2 shows an example of hardware that can be used to implement a computing device 104 and a supplemental computing device 116 shown in FIG. 1 in accordance with some aspects of the disclosed subject matter. As shown in FIG. 2, the computing device 104 can include a processor 144, a display 148, an input 152, a communication system 156, and a memory 160. The processor 144 can implement at least a portion of the image analysis application 132, which can, for example, be executed from a program (e.g., saved and retrieved from the memory 160). The processor 144 can be any suitable hardware processor or combination of processors, such as a central processing unit ("CPU"), a graphics processing unit ("GPU"), etc., which can execute a program, which can include the processes described below.

In some configurations, the display 148 can present a graphical user interface. In some configurations, the display 148 can be implemented using any suitable display devices, such as a computer monitor, a touchscreen, a television, etc. In some configurations, the inputs 152 of the computing device 104 can include indicators, sensors, actuatable buttons, a keyboard, a mouse, a graphical user interface, a touch-screen display, etc. In some configurations, the inputs 152 can allow a user (e.g., a medical practitioner, such as a neurologist) to interact with the computing device 104, and thereby to interact with the supplemental computing device 116 (e.g., via the communication network 112). The display 108 can be a display device such as a computer monitor, a touchscreen, a television, and the like.

In some configurations, the communication system 156 can include any suitable hardware, firmware, and/or software for communicating with the other systems, over any suitable communication networks. For example, the communication system 156 can include one or more transceivers, one or more communication chips and/or chip sets, etc. In a more particular example, the communication system 156 can include hardware, firmware, and/or software that can be used to establish a coaxial connection, a fiber optic connection, an Ethernet connection, a USB connection, a Wi-Fi connection, a Bluetooth connection, a cellular connection, etc. In some configurations, the communication system 156 allows the computing device 104 to communicate with the supplemental computing device 116 (e.g., directly, or indirectly such as via the communication network 112).

In some configurations, the memory 160 can include any suitable storage device or devices that can be used to store instructions, values, etc., that can be used, for example, by the processor 144 to present content using the display 148 and/or the display 108, to communicate with the supplemental computing device 116 via communications system(s) 156, etc. The memory 160 can include any suitable volatile memory, non-volatile memory, storage, or any suitable combination thereof. For example, the memory 160 can include RAM, ROM, EEPROM, one or more flash drives, one or more hard disks, one or more solid state drives, one or more optical drives, etc. In some configurations, the memory 160 can have encoded thereon a computer program for controlling operation of the computing device 104 (or the supplemental computing device 116). In such configurations, the processor 144 can execute at least a portion of the computer program to present content (e.g., user interfaces, images, graphics, tables, reports, and the like), receive content from the supplemental computing device 116, transmit information to the supplemental computing device 116, and the like.

Still referring to FIG. 2, the supplemental computing device 116 can include a processor 164, a display 168, an input 172, a communication system 176, and a memory 180. The processor 164 can implement at least a portion of the image analysis application 132, which can, for example, be executed from a program (e.g., saved and retrieved from the memory 180). The processor 164 can be any suitable hardware processor or combination of processors, such as a central processing unit (CPU), a graphics processing unit (GPU), and the like, which can execute a program, which can include the processes described below.

In some configurations, the display 168 can present a graphical user interface. In some configurations, the display 168 can be implemented using any suitable display devices, such as a computer monitor, a touchscreen, a television, etc. In some configurations, the inputs 172 of the supplemental computing device 116 can include indicators, sensors, actuatable buttons, a keyboard, a mouse, a graphical user interface, a touch-screen display, etc. In some configurations, the inputs 172 can allow a user (e.g., a medical practitioner, such as a neurologist) to interact with the supplemental computing device 116, and thereby to interact with the computing device 104 (e.g., via the communication network 112).

In some configurations, the communication system 176 can include any suitable hardware, firmware, and/or software for communicating with the other systems, over any suitable communication networks. For example, the communication system 176 can include one or more transceivers, one or more communication chips and/or chip sets, etc. In a more particular example, the communication system 176 can include hardware, firmware, and/or software that can be used to establish a coaxial connection, a fiber optic connection, an Ethernet connection, a USB connection, a Wi-Fi connection, a Bluetooth connection, a cellular connection, and the like. In some configurations, the communication system 176 allows the supplemental computing device 116 to communicate with the computing device 104 (e.g., directly, or indirectly such as via the communication network 112).

In some configurations, the memory 180 can include any suitable storage device or devices that can be used to store instructions, values, and the like, that can be used, for example, by the processor 164 to present content using the display 168 and/or the display 108, to communicate with the computing device 104 via communications system(s) 176, and the like. The memory 180 can include any suitable volatile memory, non-volatile memory, storage, or any suitable combination thereof. For example, the memory 180 can include RAM, ROM, EEPROM, one or more flash drives, one or more hard disks, one or more solid state drives, one or more optical drives, etc. In some configurations, the memory 180 can have encoded thereon a computer program for controlling operation of the supplemental computing device 116 (or the computing device 104). In such configurations, the processor 164 can execute at least a portion of the computer program to present content (e.g., user interfaces, images, graphics, tables, reports, and the like), receive content from the computing device 104, transmit information to the computing device 104, and the like.

Figure 3A:
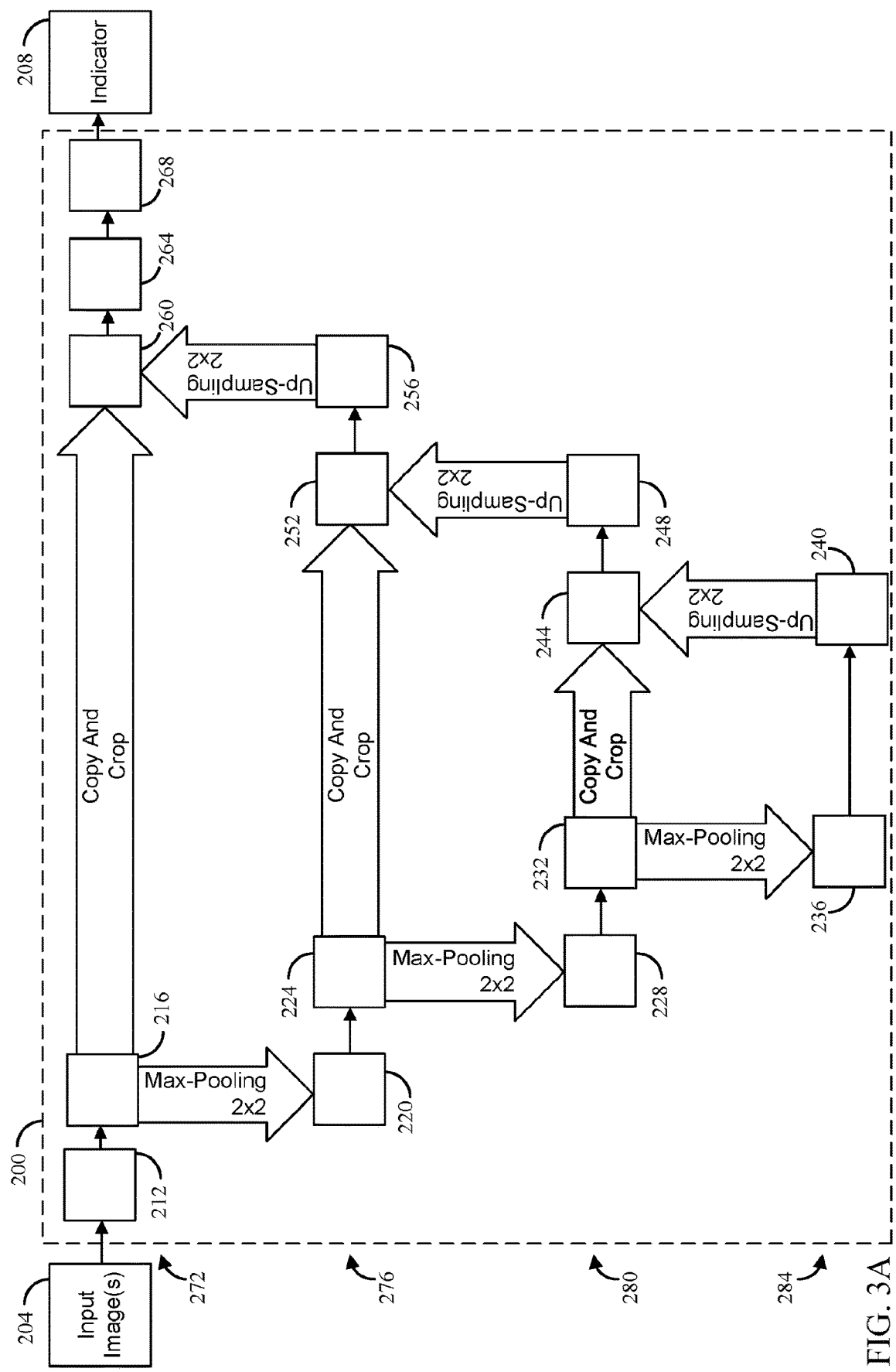
FIG. 3A is an example of a model for stroke detection.

FIG. 3A shows an example of a model 200 for stroke detection. More specifically, as shown, the model 200 can be a machine learning model. In some aspects, the model 200 can be an artificial neural network such as a convolutional neural network (CNN). The model can receive at least one input image 204 and output at least one indicator 208 based on the input image 204. In some configurations, the model 200 can be implemented in the image analysis application 132. In some configurations, the model 200 can receive the input image 204 from the image database 120 and output the indicator 208 to the analysis data database 128.

In some configurations, the input image 204 can include a DWI image. In some configurations, the indicator 208 can include a segmentation map (e.g., a binary segmentation map) indicative of locations of lesions, stroke occurrences, and/or other brain injury locations. In some configurations, the indicator 208 can include a stroke occurrence metric indicative of whether or not a stroke has occurred. In some configurations, the stroke occurrence metric can be a continuous value (e.g., selected from values ranging from 0 to 1, inclusive) or a categorical value (e.g., a "0" for no stroke having occurred and a "1" for a stroke having occurred). In some configurations, the DWI image can be a portion of a larger DWI image of an entire brain of a patient. The portion of the larger DWI image can provide sufficient image context for generating the indicator 208 while still being computationally and memory efficient.

In some configurations, the model 200 can be a two-channel convolutional neural network. In this way, the model 200 can receive multiple DWI images of the brain that are generated using different imaging parameters. For example, a first DWI image can be generated using a b value of zero, and a second DWI image can be generated using a b value of one thousand. Certain anatomical features may be better captured by different imaging parameters. Thus, the model 200 may more accurately generate an indicator (e.g., a segmentation map) using multiple DWI images of the brain generated with different imaging parameters as compared to using a single DWI image of the brain.

In some configurations, the model 200 can include a number of convolutional layers, such a three-dimensional (3D) convolutional layers. In some configurations, the model 200 can include a first convolutional layer 212, a second convolutional layer 216, a third convolutional layer 220, a fourth convolutional layer 224, a fifth convolutional layer 228, a sixth convolutional layer 232, a seventh convolutional layer 236, an eighth convolutional layer 240, a ninth convolutional layer 244, a tenth convolutional layer 248, an eleventh convolutional layer 252, a twelfth convolutional layer 256, a thirteenth convolutional layer 260, a fourteenth convolutional layer 264, and a fifteenth convolutional layer 268. In Some configurations, the model 200 can include a 3D U-Net neural network. 3D models can provide spatial information not available with a 2D model. For example, 3D models can process information along the axial plane.

In some configurations, each of the first convolutional layer 212, the second convolutional layer 216, the third convolutional layer 220, the fourth convolutional layer 224, the fifth convolutional layer 228, the sixth convolutional layer 232, the seventh convolutional layer 236, the eighth convolutional layer 240, the ninth convolutional layer 244, the tenth convolutional layer 248, the eleventh convolutional layer 252, the twelfth convolutional layer 256, the thirteenth convolutional layer 260, and the fourteenth convolutional layer 264 can include a number of filters with rectified linear unit (ReLu) activations. In some configurations, the model 200 can include a downsampling arm and an upsampling arm with horizontal connections between the downsampling arm and the upsampling arm that concatenate feature maps at different spatial scales. In some configurations, the downsampling arm can include the first convolutional layer 212, the second convolutional layer 216, the third convolutional layer 220, the fourth convolutional layer 224, the fifth convolutional layer 228, the sixth convolutional layer 232, and the seventh convolutional layer 236. In some configurations, the upsampling arm can include the eighth convolutional layer 240, the ninth convolutional layer 244, the tenth convolutional layer 248, the eleventh convolutional layer 252, the twelfth convolutional layer 256, the thirteenth convolutional layer 260, and the fourteenth convolutional layer 264.

In some configurations, the convolutional layers can include varying numbers of filters per layer. In some configurations, the first convolutional layer 212 can include thirty-two 3×3×3 filters, the second convolutional layer 216 can include sixty-four 3×3×3 filters, the third convolutional layer 220 can include sixty-four 3×3×3 filters, the fourth convolutional layer 224 can include one hundred and twenty-eight 3×3×3 filters, the fifth convolutional layer 228 can include one hundred and twenty-eight 3×3×3 filters, the sixth convolutional layer 232 can include two hundred and fifty-six 3×3×3 filters, the seventh convolutional layer 236 can include two hundred and fifty-six 3×3×3 filters, the eighth convolutional layer 240 can include five hundred and twelve 3×3×3 filters, the ninth convolutional layer 244 can include five hundred and twelve 3×3×3 filters, the tenth convolutional layer 248 can include two hundred and fifty-six 3×3×3 filters, the eleventh convolutional layer 252 can include two hundred and fifty-six 3×3×3 filters, the twelfth convolutional layer 256 can include one hundred and twenty-eight 3×3×3 filters, the thirteenth convolutional layer 260 can include one hundred and twenty-eight 3×3×3 filters, the fourteenth convolutional layer 264 can include sixty-four 3×3×3 filters, and the fifteenth convolutional layer 268 can include one 1×1×1 filter.

The first convolutional layer 212 can apply a number of filters to the input image(s) 204 and output a number of feature maps to the second convolutional layer 216. The second convolutional layer 216 can apply a number of filters to the feature maps from the first convolutional layer 212 to generate a number of feature maps. The model 200 can copy and crop the feature maps, and transmit the feature maps to the fourteenth convolutional layer 260. The model 200 can also max-pool the feature maps generated by the second convolutional filter 216 with a 2×2 filter to generate a max pool feature map, and transmit the max-pool feature map to the third convolutional layer 220.

The third convolutional layer 220 can apply a number of filters to the input max pool feature map, and output a number of feature maps to the fourth convolutional layer 224. The fourth convolutional layer 224 can apply a number of filters to the feature maps from the third convolutional layer 220 to generate a number of feature maps. The model 200 can copy and crop the feature maps, and transmit the feature maps to the twelfth convolutional layer 252. The model 200 can also max-pool the feature maps generated by the fourth convolutional filter 224 with a 2×2 filter to generate a max pool feature map, and transmit the max-pool feature map to the fifth convolutional layer 228.

The fifth convolutional layer 228 can apply a number of filters to the input max pool feature map, and output a number of feature maps to the sixth convolutional layer 232. The sixth convolutional layer 232 can apply a number of filters to the feature maps from the fifth convolutional layer 228 to generate a number of feature maps. The model 200 can copy and crop the feature maps, and transmit the feature maps to the tenth convolutional layer 244. The model 200 can also max-pool the feature maps generated by the sixth convolutional filter 232 with a 2×2 filter to generate a max pool feature map, and transmit the max-pool feature map to the seventh convolutional layer 236.

The seventh convolutional layer 236 can apply a number of filters to the input max pool feature map, and output a number of feature maps to the eighth convolutional layer 240. The eighth convolutional layer 240 can up-sample the feature maps generated by the seventh convolutional layer 236 to generate an up-sampled feature map using a 2×2 filter, and transmit the up-sampled feature map to the tenth convolutional layer 244.

The tenth convolutional layer 244 can apply a number of filters to the up-sampled feature map from the ninth convolutional layer 240 and the feature maps from the sixth convolutional filter 232 to generate a number of feature maps. The model 200 can output the feature maps to the eleventh convolutional layer 248. The eleventh convolutional layer 248 can up-sample the feature maps generated by the tenth convolutional layer 244 to generate an up-sampled feature map using a 2×2 filter, and transmit the up-sampled feature map to the twelfth convolutional layer 252.

The twelfth convolutional layer 252 can apply a number of filters to the up-sampled feature map from the eleventh convolutional layer 248 and the feature maps from the fourth convolutional filter 224 to generate a number of feature maps. The model 200 can output the feature maps to the thirteenth convolutional layer 256. The thirteenth convolutional layer 256 can up-sample the feature maps generated by the twelfth convolutional layer 252 to generate an up-sampled feature map using a 2×2 filter, and transmit the up-sampled feature map to the fourteenth convolutional layer 260.

The fourteenth convolutional layer 260 can apply a number of filters to the up-sampled feature map from the thirteenth convolutional layer 256 and the feature maps from the second convolutional filter 216 to generate a number of feature maps. The model 200 can output the feature maps to the fifteenth convolutional layer 264. The fifteenth convolutional layer 264 can apply a 1×1×1 filter to the feature maps, and generate the indicator 208. In some configurations, the fifteenth convolutional layer can include sigmoid activations. As described above, in some configurations, the indicator 208 can include segmentation map. In some configurations, the segmentation map can be a 3D segmentation map. In some configurations, the model 200 can determine if the segmentation map output by the fifteenth convolutional layer 264 includes a predetermined number (e.g., one, three, five, etc.) of pixels that indicate a location of a lesion, a stroke occurrence, and/or other another brain injury. For example, if at least two pixels indicate occurrence of a stroke (e.g., are a "1"), the model 200 can output a single brain injury value indicative of the occurrence of a stroke.

In some configurations, the model 200 can include a number of spatial scales, such as a first spatial scale 272, a second spatial scale 276, a third spatial scale 280, and a fourth spatial scale 284. Each spatial scale can include a number of the convolutional layers that have approximately the same spatial resolution (e.g., size in the X, Y, and Z dimensions). In some configurations, the first spatial scale 272 can include the first convolutional layer 212, the second convolutional layer 216, the thirteenth convolutional layer 260, and the fourteenth convolutional layer 264, the second spatial scale 276 can include the third convolutional layer 220, the fourth convolutional layer 224, the eleventh convolutional layer 252, and the twelfth convolutional layer 256, the third spatial scale 280 can include the fifth convolutional layer 228, the sixth convolutional layer 232, the ninth convolutional layer 244, and the tenth convolutional layer 248, and the fourth spatial scale 284 can include the seventh convolutional layer 236 and the eighth convolutional layer 240.

Referring now to FIG. 3A as well as FIG. 3B, an example of an inception module 300 for use with the model 200 is shown. In some configurations, the inception model 200 can include an inception module 300 from Inception-V4 architecture. The inception module 300 can include multiple pathways with different convolutional filter sizes, which can allow the model 200 to learn from a variety of field-of-views. The inception module 300 can receive input 304 (e.g., one or more feature maps) from a previous convolutional layer and generate an output 340 (e.g., one or more feature maps) based on the input 304.

In some configurations, the inception module 300 can include a first pathway including a convolutional layer 320. In some configurations, the convolutional layer 320 can include a 1×1 convolutional filter with ReLu activation.

In some configurations, the inception module 300 can include a second pathway including a first convolutional layer 308 that can feed into a second convolutional layer 324. In some configurations, the first convolutional layer 308 can include a 1×1 convolutional filter with ReLu activation. In some configurations, the second convolutional layer 324 can include a 3×3 convolutional filter with ReLu activation.

In some configurations, the inception module 300 can include a third pathway including a first convolutional layer 312 that can feed into a second convolutional layer 328. The second convolutional layer 328 can feed into a third convolutional layer 336 included in the third pathway. In some configurations, the first convolutional layer 312 can include a 1×1 convolutional filter with ReLu activation. In some configurations, the second convolutional layer 328 can include a 3×3 convolutional filter with ReLu activation. In some configurations, the third convolutional layer 336 can include a 3×3 convolutional filter with ReLu activation.

In some configurations, the inception module 300 can include a fourth pathway including an average pooling layer 316 that can feed into a convolutional layer 332. In some configurations, the convolutional layer 332 can include a 1×1 convolutional filter with ReLu activation.

The pathways can output a number of feature maps to be used as the output 340. More specifically, the output 340 can include feature maps output from the convolutional layer 320 in the first pathway, the second convolutional layer 324 in the second pathway, the third convolutional layer 336 in the third pathway, and the convolutional layer 332 in the fourth pathway. In some configurations, the output 340 can include the feature maps output from the convolutional layer 320 in the first pathway, the second convolutional layer 324 in the second pathway, the third convolutional layer 336 in the third pathway, and the convolutional layer 332 in the fourth pathway concatenated as a single feature map.

In some configurations, the model 200 in FIG. 3A can include a number of inception modules (e.g., the inception module 300) in the each of the convolutional layers. In some configurations, the inception module 300 can be included in place of each convolutional filter (e.g., 3×3×3 filter) in each of the first convolutional layer 212, the second convolutional layer 216, the third convolutional layer 220, the fourth convolutional layer 224, the fifth convolutional layer 228, the sixth convolutional layer 232, the seventh convolutional layer 236, the eighth convolutional layer 240, the ninth convolutional layer 244, the tenth convolutional layer 248, the eleventh convolutional layer 252, the twelfth convolutional layer 256, the thirteenth convolutional layer 260, and the fourteenth convolutional layer 264 can be replaced by the inception module 300. For example, the first convolutional layer 212 can include thirty-two inception modules, each inception module being the inception module 300 in FIG. 3B.

Referring now to FIG. 3A as well as FIG. 3C, an example of a residual connection 344 is shown. The residual connection 344 can allow a convolutional layer to be skipped. For example, a first convolutional layer 348 can output generated feature maps to a third convolutional layer 356 rather than a second convolutional layer 352 using the residual connection, thereby skipping the second convolutional layer 352. In some configurations, the model 200 in FIG. 3A can include at least one of the residual connection 344. In some configurations, the residual connections may only exist between convolutional layers included in the same spatial scale in the model 200. For example, the first spatial scale 272 can include residual connections between the first convolutional layer 212, the second convolutional layer 216, the thirteenth convolutional layer 260, and the fourteenth convolutional layer 264, without any residual connections to convolutional layers in the second spatial scale 276, the third spatial scale 280, and the fourth spatial scale 284.

Referring now to FIG. 3A as well as FIG. 3D, an example of a dense connection 360 is shown. The dense connection 360 can allow feature maps from every convolutional layer to be carried into successive layers. In some configurations, the dense connection 360 can have a growth rate of two. In some configurations, the model 200 in FIG. 3A can include at least one of the residual connection 344. In some configurations, the dense connections may only exist between convolutional layers included in the same spatial scale in the model 200. For example, the first spatial scale 272 can include dense connections between the first convolutional layer 212, the second convolutional layer 216, the thirteenth convolutional layer 260, and the fourteenth convolutional layer 264, without any dense connections to convolutional layers in the second spatial scale 276, the third spatial scale 280, and the fourth spatial scale 284.

Referring now to FIG. 3A as well as FIG. 3E, an example of a squeeze-and-excitation module 376 is shown. The squeeze-and-excitation module 376 can learn relationships between different feature maps at different layers of the neural network by rescaling a layer with compressed feature maps from the previous layer. In some configurations, the squeeze-and-excitation module 376 can have a reduction ratio of sixteen, which can reduce computational complexity.

The squeeze-and-excitation module 376 can include a number of cascading layers with different activation techniques. For example, squeeze-and-excitation module 376 can include a global pooling layer 382.

Referring now to FIGS. 3A-3E, in some configurations, the model 200 can be included as a portion of an ensemble model having multiple sub models (e.g., multiple neural networks). In some configurations, the ensemble model can include submodels modified to include at least one of the modules and/or connections shown in FIGS. 3B-3E. For example, the ensemble model can include a submodel including inception modules (e.g., the inception module 300) and another submodel including residual connections (e.g., the residual connection 344).

In some configurations, the ensemble model can include multiple submodels having the same architecture. For example, the ensemble model can include a first submodel including inception modules and a second submodel including inception modules. In some configurations, the second submodel can be trained using a boosting method. More specifically, the second submodel can be trained with the weights initialized from the first submodel. In some configurations, each submodel can be trained individually (e.g., using a bagging technique).

Figure 4:
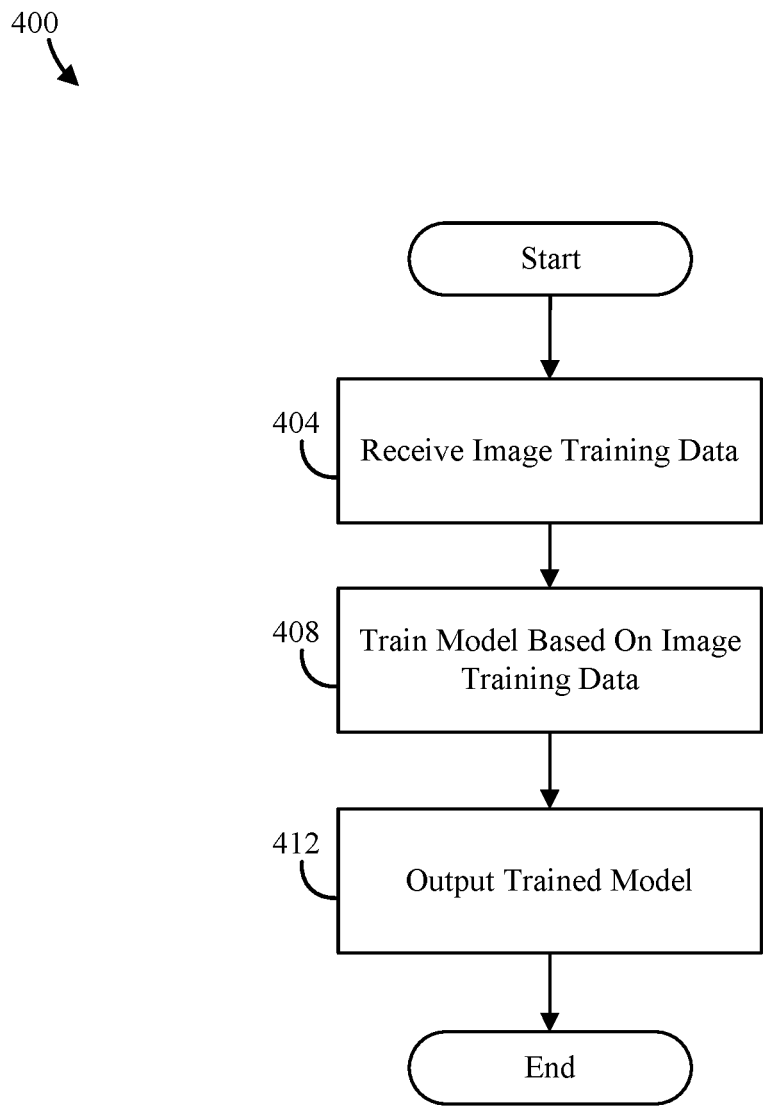
FIG. 4 is an exemplary process for training the model in FIG. 3A.

Referring now to FIG. 3 as well as FIG. 4, an exemplary process 400 for training the model 200 is shown. The process 400 can be used to train the model 400 to classify pixels of an input image as lesions or not lesions. The process 400 can be included in the image analysis application 132.

At 404, the process 400 can receive image training data. In some configurations, the image training data can include a number of DWI images of at least a portion of a brain of a patient. The imaging training data may be included in the training data database 124. In some configurations, a portion of the DWI images can be generated using a predetermined set of imaging parameters (e.g. a b value of one thousand and a 1.5T imaging system), and another portion of the DWI images can be generated using a different predetermined set of imaging parameters (e.g. a b value of zero and a 1.5T imaging system). In some configurations, a predetermined portion of the DWI images can be associated with the presence of a lesion, and the remaining portion of the DWI images can be associated with the lack of a lesion. In some configurations, about fifty percent of the DWI images can be associated with the presence of a lesion and/or ischemic stroke, and the remaining DWI images can be associated with the lack of a lesion and/or ischemic stroke.

The image training data can also include a number of annotations associated with a portion of the DWI images generated using the same imaging parameters. The annotations can include outlined segments of the DWI images that contain lesions. A number of human practitioners can provide the annotations. In some configurations, the annotations can be associated with the DWI images generated using a b value of one thousand. Many human practitioners have experience in outlining lesions on DWI images produced with a b value of one thousand. It is noted that the model 200 may not require annotations for DWI images generated using different imaging parameters. For example, the image training data can only include annotations associated with the DWI images produced with a b value of one thousand, and no annotations associated with the DWI images produced with a b value of zero.

In some configurations, the DWI images can be a portion of a larger DWI image (e.g., a patch of the total brain DWI image). For example, the DWI image can be a 64×64×8 pixel image patch, with each pixel representing a one cubic millimeter voxel. The patch can provide enough image context for segmentation while still being computationally and memory efficient. In order to segment an entire DWI image, multiple patches of the DWI image can be provided to the model once the model is trained.

In some configurations, the DWI images can be preprocessed to zero mean and unit variance. It is noted that, in some configurations, the DWI images may not be resampled in order to avoid introducing any resampling errors in the image and/or the associated annotation. Furthermore, in some configurations, brain extraction may not be performed on the DWI images because in testing, the model was shown to accurately segment stroke lesions without brain extraction preprocessing.

In some configurations, each of the images can be included in either a training set, a validation set, or a testing set. In some configurations, to prevent overfitting and to increase the size of the training set, the process 400 can augment patches using sagittal flips.

At 408, the process 400 can train the model 200 based on the image training data. For each image frame included in the image training data, the process 400 can provide the image frame to the model 200 as an input image (e.g., the input image 204) and an associated annotation to the model 200. The annotation can function as a ground truth in training the model 200 to identify and/or segment regions of input images associated with lesions. As mentioned above, in some configurations, the model 200 can receive two images. In such configurations, the process 400 can provide two images and an annotation associated with at least one of the two images to the model 200. For example, the process 400 can provide a DWI image with a b value of one thousand, a DWI image with a b value of zero, and an annotation associated with the DWI image with a b value of one thousand to the model 200.

In some configurations, the process 400 can train the model 200 using Nestorov Adaptive Moment Estimation (Nadam) with an initial learning rate 10-5, minimizing a soft Dice loss function:

$$D(q, p) = \frac{2\sum_i p_i q_i}{\sum_i (p_i + q_i) + \alpha} \quad (1)$$

where D is Sorensen-Dice coefficient, q is the probability output of the neural network, p is the ground truth, and $\alpha$ is a smoothing constant set to 1. In some configurations, the process 400 can provide each of the images in the training set both forward and backwards for an epoch, and evaluate model performance on the validation set following the epoch. In some configurations, the calculate soft dice using equation (1) on the validation set following each epoch. In some configurations, the process 400 can determine the model 200 is trained if the soft dice does not improve for ten consecutive epochs.

At 412, the process 400 can output the trained model 200. In some configurations, the process 400 can cause the trained model 200 to be saved to a memory, such as the memory 160 and/or the memory 180 in FIG. 2.

Figure 5:
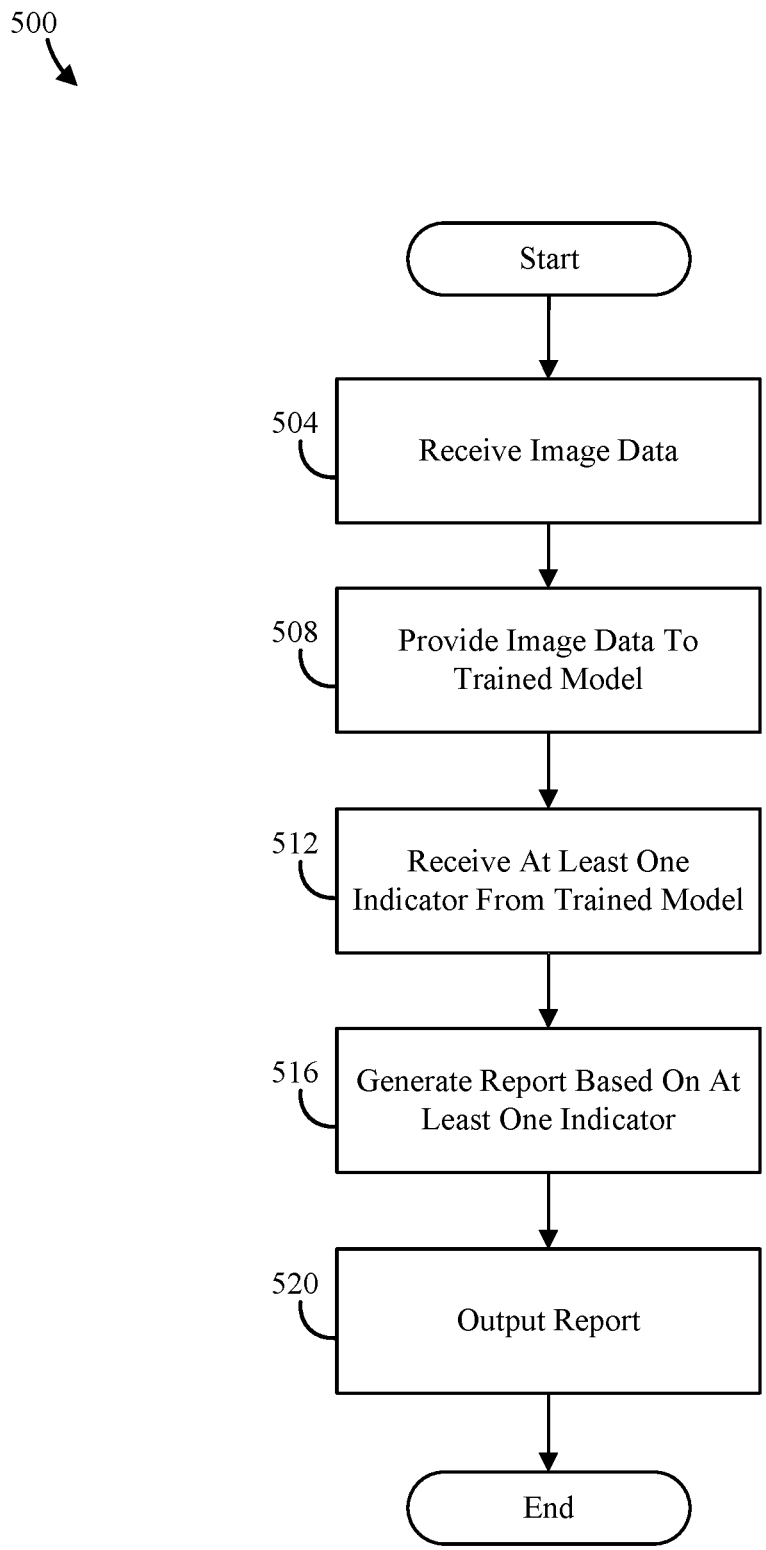
FIG. 5 is an exemplary process for automatically analyzing image data.

Referring now to FIGS. 1 and 3, as well as FIG. 5, an exemplary process 500 for automatically analyzing image data, such as DWI images of a patient brain, is shown. The image analysis application 132 can include the process 500.

At 504, the process 500 can receive image data. In some configurations, the image data can include a number of DWI images of at least a portion of a brain of a patient. In some configurations, a portion of the DWI images can be generated using a predetermined set of imaging parameters (e.g. a b value of one thousand and a 1.5T imaging system), and another portion of the DWI images can be generated using a different predetermined set of imaging parameters (e.g. a b value of zero and a 1.5T imaging system).

In some configurations, the DWI images can be a portion of a larger DWI image (e.g., a patch of the total brain DWI image). For example, a DWI image can be a 64×64×8 pixel image patch, with each pixel representing a one cubic millimeter voxel. In some configurations, the DWI images can be preprocessed to zero mean and unit variance. In some configurations, the process 500 can process the DWI images to zero mean and unit variance at 504. It is noted that, in some configurations, the DWI images may not be resampled in order to avoid introducing any resampling errors in the image and/or the associated annotation. Furthermore, in some configurations, brain extraction may not be performed on the DWI images because in testing, the model was shown to accurately segment stroke lesions without brain extraction preprocessing.

At 508, the process 500 can provide the image data to a trained model. In some configurations, the trained model can be the model 200 trained using the process 400 in FIG. 4. In some configurations, the process 500 can provide a single DWI image patch to the trained model. In some configurations, the process 500 can provide a sequence of overlapping DWI image patches to the trained model. In some configurations, each pixel included in the DWI image of the brain can be included in at least one of the DWI image patches, with some pixels included in the DWI image of the brain can be included in multiple DWI image patches. In some configurations, the process 500 can determine the sequence of overlapping DWI image patches using a predetermined overlap ratio. For example, patches can be considered neighbors if the patches have an overlap ratio of 15/16. The sequence can include every neighboring patch in the overall DWI image. In some configurations, each DWI image patch can be smaller than the patch size used to train the model. For example, if the model is trained using a patch size of 64×64×8, each DWI image patch can have a patch size of 62×62×6. The smaller patch size and overlap ratio can help mitigate edge effects.

In some configurations, the process 500 can determine a sequence of neighboring image patches for each portion of the DWI images generated using different imaging parameters (e.g. different b values). Patches associated with the same spatial area in each sequence can be provided to the trained model at the same time.

At 512, the process 500 can receive at least one indicator from the trained model. In some configurations, the process 500 can receive a probability map associated with each image patch provided to the trained model. In two-channel configurations, the process 500 can receive a single probability map for each pair of DWI image patches input to the trained model. Each probability map can be associated with the same spatial area as the input DWI image patch used to generate the probability map. The probability map can include a three-dimensional matrix of probability values, which can be continuous values (e.g., selected from values ranging from 0 to 1, inclusive).

At 516, the process 500 can generate a report based on the at least one indicator. In some configurations, for each pixel in the overall DWI image of the brain, the process 500 can average the probability values included in the probability maps that are associated with the pixel. The averaged probability values can be included in a final probability map, which can be the size of the overall DWI image. In some configurations, the process 500 can binarize the probability values to either zero or one, with zero indicating lack of a lesion and one indicating the presence of a lesion, based on a threshold value. In some configurations, the process 500 can set each pixel in the final probability map to one if the average probability value greater than or equal to the threshold value (e.g., 0.5), and zero otherwise. Following the binarization, the final probability map can be referred to as a segmentation map. In some configurations, the report can include the raw segmentation map.

In some configurations, the report can include a stroke occurrence metric indicative of whether a stroke has occurred in the patient or not. In some configurations, the stroke occurrence metric can be a categorical value (e.g., "stroke has occurred" or "stroke has not occurred"). In some configurations, the process 500 can determine if at least one pixel in the segmentation map is indicative of the presence of a lesion (e.g., a binarized probability value of one). If the at least one pixel in the segmentation map is indicative of the presence of a lesion, the stroke occurrence metric can be set to "stroke has occurred," or "stroke has not occurred" otherwise.

In some configurations, the report can include a slice of the overall DWI image with the highest number of pixels indicative of the presence of a lesion. In some configurations, the pixels indicative of the presence of a lesion can be outlined, highlighted, or otherwise distinguished from the pixels indicative of the lack of a lesion, which can be helpful if the report is displayed on a screen for viewing by a medical practitioner (e.g., a neurologist).

In some configurations, the report can include a volume of lesions in the brain of the patient. The volume can be determined based on the size of a voxel in the brain associated with each pixel in the segmentation map.

At 520, the process 500 can output the report to at least one of a memory or a display. In some configurations, at 520, the process 500 can cause the report to be displayed on a display (e.g., the display 108, the display 148 in the computing device 104, and/or the display 168 in the supplemental computing device 116). In some configurations, at 520, the process 500 can cause the report to be saved to memory (e.g., the memory 160, in the computing device 104 and/or the memory 180 in the supplemental computing device 116).

The image analysis application 132 can include the process 400 in FIG. 4 and process 500 in FIG. 5. The processes 400 and 500 may be implemented as computer readable instructions on a memory or other storage medium and executed by a processor.

Experiments

The patient cohort included 1,205 consecutive patients with DWI-confirmed acute ischemic stroke from the NIH-funded Heart-Brain Interactions in Human Acute Ischemic Stroke Study, recruited between June 2009 and December 2011. One investigator blinded to DWI findings performed outcome assessments through in person evaluations, phone interviews, or reviews of physician notes obtained during outpatient visits when the patient was unavailable for a follow-up visit. Follow-up evaluation included assessment of survival and functional outcome using modified Rankin Score dichotomized as good (mRS<=2) and bad (mRS>2) outcome at 90±15 days.

DWI (b-value=0, b0, and 1000 s/mm$^2$, b1000) was performed on 1.5T General Electric (Milwaukee, WI) and 1.5T Siemens (Erlangen, Germany) MR instruments. The full diffusion tensor was sampled using a single-shot echo-planar imaging (EPI) technique repeated in at least six non-collinear diffusion gradient directions. The resolution in the x-y plane ranged from 0.859-1.72 mm and the resolution in the z plane ranged from 6-6.5 mm. Expert manual annotations of acute infarcts were generated using an image outlining software (MRICron, United States) by a vascular neurologist. All outlines were adjudicated by a senior stroke neurologist and final outlines were generated. The patients were randomly divided into Training (n=720), Validation (n=243), and Testing (n=242) sets in a 3:1:1 ratio. The Training Set was used to train our deep-learning algorithm and the performance of Validation Set was evaluated to assess for under/overfitting. Training was stopped when performance on the Validation Set no longer improved. The Testing Set was used for evaluation of segmentation quality once the model was finalized to ensure generalizability of the trained model.

TABLE 1

| | |
|---|---|
| Age (median years, IQR) | 70 (55-81) |
| Female gender (%) | 55 |
| Hypertension (%) | 72 |
| Diabetes mellitus (%) | 25 |
| History of prior stroke or transient ischemic attack (%) | 27 |
| Congestive heart failure (%) | 6 |
| Coronary artery disease (%) | 21 |
| Admission NIHSS (median, IQR) | 4 (1-10) |
| Time from stroke onset to MRI (median hours, IQR) | 9 (5, 22) |
| Etiologic CCS subtype (%) | |
| Large artery atherosclerosis | 21 |
| Cardiac embolism | 48 |
| Small artery occlusion | 12 |
| Uncommon causes | 8 |
| Undetermined causes | 12 |
| 90-day outcome | |
| Good functional outcome (mRS <= 2, %) | 63 |
| Poor functional outcome (mRS > 2, %) | 21 |
| Death % | 16 |
| Modified Rankin Score (median, IQR) | 2 (1-4) |

Data Pre-Processing for Segmentation

For pre-processing, the intensity of each b0 and b1000 DWI image was normalized to zero mean and unit variance. Notably, the images were not resampled in order to avoid introducing any resampling errors in both the image and manual segmentations. Furthermore, brain extraction was not applied to the images, after observing that our neural networks can accurately segment the stroke lesions without this preprocessing step.

Neural Network Architecture for Segmentation

A 3D neural network architecture was utilized, implemented within the DeepNeuro framework. The architecture comprises a downsampling and an upsampling arm with horizontal connections between the two that concatenate feature maps at different spatial scales. The rectified linear unit (ReLu) activation was used in all layers, with the exception of the final sigmoid output. Batch normalization was applied after each convolutional layer for regularization. Nestorov Adaptive Moment Estimation (Nadam) was used to train the models with an initial learning rate 10-5, minimizing a soft Dice loss function in Equation (1) above. α is a smoothing constant set to 1 in the present experiment.

Because lesion segmentation is a challenging problem, modifications of the base model shown in FIG. 3A (e.g., the model 200 without any of the modules and/or connections in FIGS. 3B-3C architectures were investigated. Specifically, residual connections, inception modules, dense connections, and squeeze-and-excitation modules (FIGS. 3B-E) were individually into the model 200, all of which are state-of-the-art components that have improved neural network architectures for classification tasks in the past. In this experiment, a 3D U-Net architecture was used as the base model.

Residual connections are "shortcut" connections that allow for skipping of convolution layers. Inception modules have multiple pathways with different convolution filter sizes, allowing the network to learn from a variety of field-of-views. Here, inception modules from the Inception-V4 architecture were utilized. Dense connections allow feature maps from every convolutional layer to be carried into successive layers. Dense connections with a growth rate of two were used in place of each block of convolutions. Squeeze-and-excitation modules with a reduction ratio of 16 was utilized to reduce the computational complexity. These components were added to the 3D U-Net individually to devise four new neural network architectures (Residual U-Net, Inception U-Net, Dense U-Net, and Squeeze-and-Excitation U-Net). The components were added to each convolutional layer within each spatial scale and did not carry past the consequent downsampling or upsampling layers.

Twenty patches of size 64×64×8 mm voxels were extracted for each patient in the training set. Two channels were used, one for the b0 DWI image and one for the b1000 DWI image. The chosen patch size provided enough image context for segmentation while still being computationally and memory efficient. Patches were extracted from non-ischemic and ischemic esions in a 1:1 ratio. To prevent overfitting and to increase the size of the training set, patches were augmented by means of sagittal flips. Our networks were implemented in DeepNeuro with Keras and TensorFlow backend. The network was trained iteratively through all extracted patches on a NVIDIA Tesla P100 graphics processing unit. Four patches were extracted for each patient in the Validation Set and the soft dice was evaluated at the end of each training epoch. Training was stopped when Validation Set soft dice did not improve for ten consecutive epochs. Once the network was trained, inference of new DWI images was performed by inputting successive patches of size 62×62×6, with neighboring patches having an overlap ratio of 15/16. The smaller patch size and overlap criteria at inference time was used to mitigate any edge effects. Probability maps for each of these patches were then predicted by the model, and voxels with predictions from multiple overlapping patches had their probabilities averaged. Binary segmentation maps were generated by binarizing the probability maps at a threshold of 0.5. The performance of model ensembles was also evaluated. The Top 2, Top 3, and Top 4 models with different neural network architectures based on Testing Set Dice Similarity Coefficient as well as all 5 models were ensembled by averaging the output probability maps. The averaged probability maps were then binarized at a threshold of 0.5. Four additional Inception U-Nets were trained and the performance of an ensemble of 2, 3, 4, and 5 Inception U-Nets was assessed.

Qualitative Assessment by Expert Stroke Neurologist and Neuroradiologist

To qualitatively assess the quality of the stroke segmentations, 94 segmentations annotated by either a vascular neurologist or the algorithm were randomly selected. The axial slice with the largest lesion area was then determined. The segmentations were then overlaid on the b1000 DWI images and assessed by an expert stroke neurologist (H. A., Rater 1, 28 years of clinical experience), expert neuroradiologist (O. R., Rater 2, 19 years of clinical experience), and expert radiologist (M. W., Rater 3, 23 years of clinical experience) blinded to whether the segmentations were performed manually or automatically. Specifically, the expert was asked to answer 3 questions: 1) Would you edit the segmentation? 2) What is the quality of the segmentation on a scale of 1-4? 3) Was it a human annotator (as opposed to the algorithm)?

Statistical Analysis

The performance of individual models and model ensembles were evaluated by means of Testing Set Sorensen-Dice Similarity Coefficient with the Mann-Whitney U test. Additionally, the Dice Similarity Coefficient was assessed for patients with small and large infarct volumes, defined as patients with manual volumes below and above the median manual volume for all patients, respectively. Spearman's rank correlation coefficient (p) was used to evaluate the relationship between dice coefficient, manual volume, and time to MR imaging (from stroke onset). The stroke detection rate, defined as the percentage of patients with at least one true positive voxel, was calculated, as well as the lesion detection rate, defined as the percentage of lesions with at least one true positive voxel. Relatedness between volumes derived from manual and automatic segmentations was assessed via Intraclass Correlation Coefficient from one-way analysis of variance (R version 3.1.2). To compare similarity between manual and automatic segmentations, the Chi-squared test (Questions 1 and 3) and Mann-Whitney U test (Question 2) were utilized. Manual vs automatic volumes were also evaluated for patients stratified by the mRS at 90-days after admission for ischemic stroke. Volumes for mRS<=2 and >2 (excluding mRS values of 6) were compared, which represents 90-day functional outcome. mRS<=5 and equal to 6, which represents 90-day survival, were also compared. The volumes between the different mRS stratifications were evaluated using the Mann-Whitney U test. The threshold for significance for all statistical tests was p=0.05.

Results

The study cohort comprised of 1205 consecutive patients with acute ischemic stroke. Patient demographics and stroke characteristics are shown in Table 1. There were a total of 5142 infarcts in 1205 patients, with infarct volumes falling into a wide range of values from 0.004 to 818.120 mL. Training, validation, and testing datasets included 720, 243, and 242 patients, respectively.

Performance of Individual Deep Learning Models for Segmentation

The performance of the five architectures (U-Net, Residual U-Net, Inception U-Net, Dense U-Net, and Squeeze-And-Excitation U-Net) was investigated on the Testing Set. The best performing individual model was the Inception U-Net, which had a median dice similarity coefficient of 0.72 (0.697-0.751) within the Testing Set (Table 2). Notably, the performance of Inception U-Net was better than the standard U-Net (p<0.05) within the Testing Set.

TABLE 2

|  | Training Set (n = 720) | Validation Set (n = 243) | Testing Set (n = 242) |
| --- | --- | --- | --- |
| U-Net | 0.715 (0.689-0.731) | 0.691 (0.658-0.731) | 0.680 (0.626-0.714) |
| Residual U-Net | 0.709 (0.685-0.734) | 0.673 (0.633-0.723) | 0.678 (0.615-0.707) |
| Inception U-Net | 0.740 (0.721-0.765) | 0.725 (0.693-0.751) | 0.72 (0.697-0.751) |
| Dense U-Net | 0.693 (0.666-0.717) | 0.701 (0.658-0.733) | 0.696 (0.643-0.718) |
| Squeeze-And-Excitation U-Net | 0.696 (0.667-0.72) | 0.667 (0.630-0.694) | 0.650 (0.599-0.688) |

Performance of Ensembles of Different U-Net Architectures

We also assessed the performance of ensembling the individual models of different U-Net architectures. The median dice similarity coefficient on the Testing Set for an Ensemble of Top 3 Models, Ensemble of Top 4 Models, and Ensemble of All 5 Models was 0.724 (0.682-0.753), 0.722 (0.694-0.746), and 0.71 (0.686-0.738), respectively (Table 3). The best performing ensemble was the Ensemble of Top 2 Models (Inception and Dense U-nets), which had a median dice similarity coefficient of 0.726 (0.68-0.747) within the Testing Set. This performance was significantly better than that of a single U-Net ($p<0.05$) but not from a single Inception U-Net.

TABLE 3

|  | Training Set (n = 720) | Validation Set (n = 243) | Testing Set (n = 242) |
| --- | --- | --- | --- |
| Ensemble of Top 2 | 0.737 (0.715-0.757) | 0.733 (0.698-0.763) | 0.726 (0.680-0.747) |
| Ensemble of Top 3 | 0.738 (0.717-0.753) | 0.731 (0.707-0.760) | 0.724 (0.682-0.753) |
| Ensemble of Top 4 | 0.737 (0.719-0.756) | 0.723 (0.690-0.752) | 0.722 (0.694-0.746) |
| Ensemble of All 5 | 0.733 (0.712-0.751) | 0.719 (0.689-0.743) | 0.71 (0.686-0.738) |

Performance of Ensembles of Inception U-Nets

Additionally, the performance of ensembling Inception U-Nets was assessed. Within the Testing Set, the median dice similarity coefficient of the Ensemble of 2, 3, and 4 Inception U-Nets was 0.729 (0.696-0.753), 0.734 (0.708-0.75), and 0.737 (0.708-0.765) (Table 4). Notably, the performance of all ensembles of Inception U-Nets were higher than that of a Single Inception U-Net. The best performing ensemble was that of 4 Inception U-Nets. Example manual and automatic segmentations from the Ensemble of 4 Inception U-Nets are shown in FIG. 4A. This performance was significantly better than that of a single U-Net ($p<0.005$) but not from a single Inception U-Net ($p=0.18$).

TABLE 4

|  | Training Set (n = 720) | Validation Set (n = 243) | Testing Set (n = 242) |
| --- | --- | --- | --- |
| Inception U-Net | 0.740 (0.721-0.765) | 0.725 (0.693-0.751) | 0.720 (0.697-0.751) |
| Ensemble of 2 | 0.764 (0.740-0.778) | 0.739 (0.702-0.774) | 0.729 (0.696-0.753) |
| Ensemble of 3 | 0.758 (0.742-0.777) | 0.741 (0.713-0.77) | 0.734 (0.708-0.75) |
| Ensemble of 4 | 0.765 (0.749-0.781) | 0.746 (0.721-0.774) | 0.737 (0.708-0.765) |

Figure 6A:
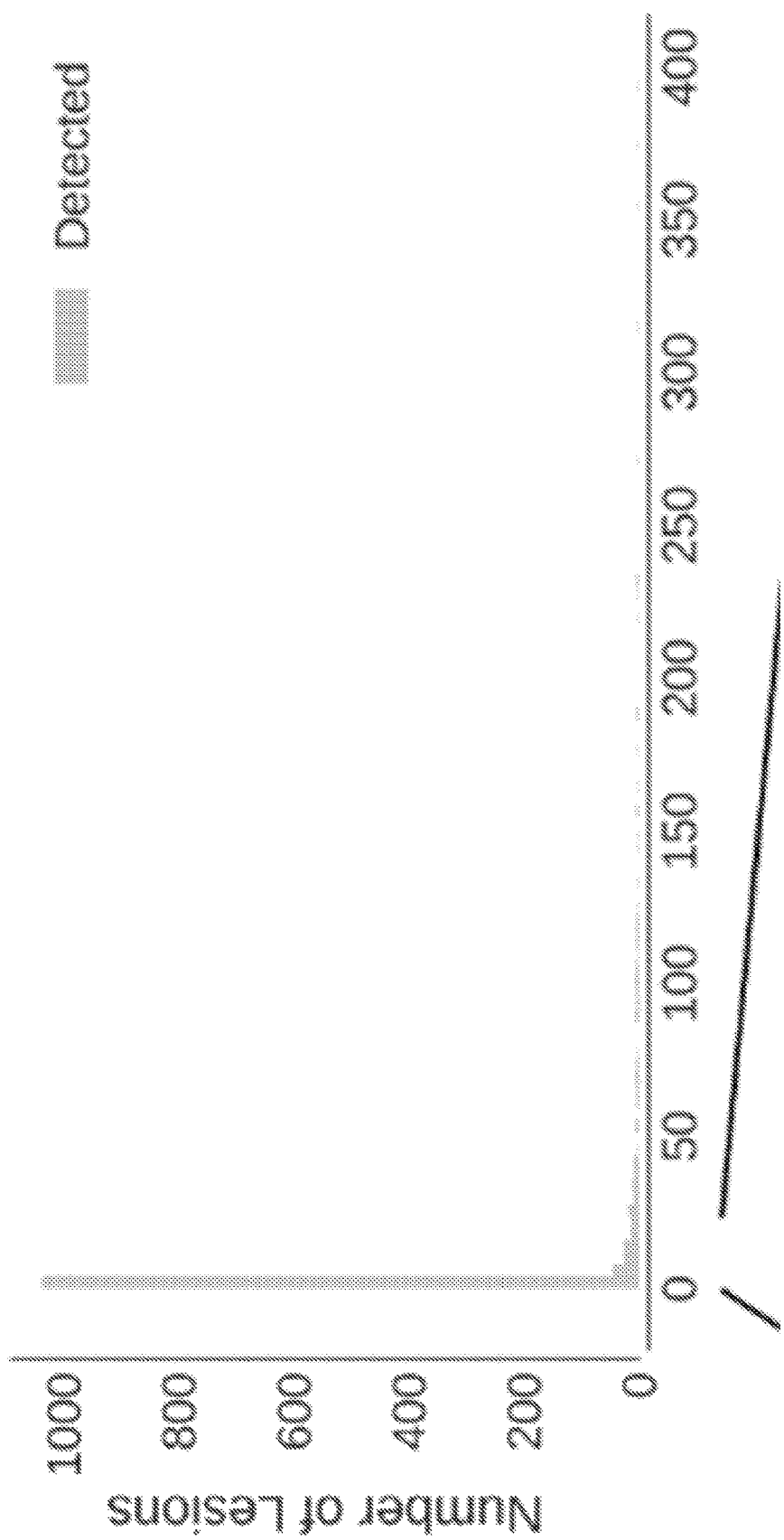
FIG. 6A is a histogram of manual lesion volumes for detected lesions.
Figure 6B:
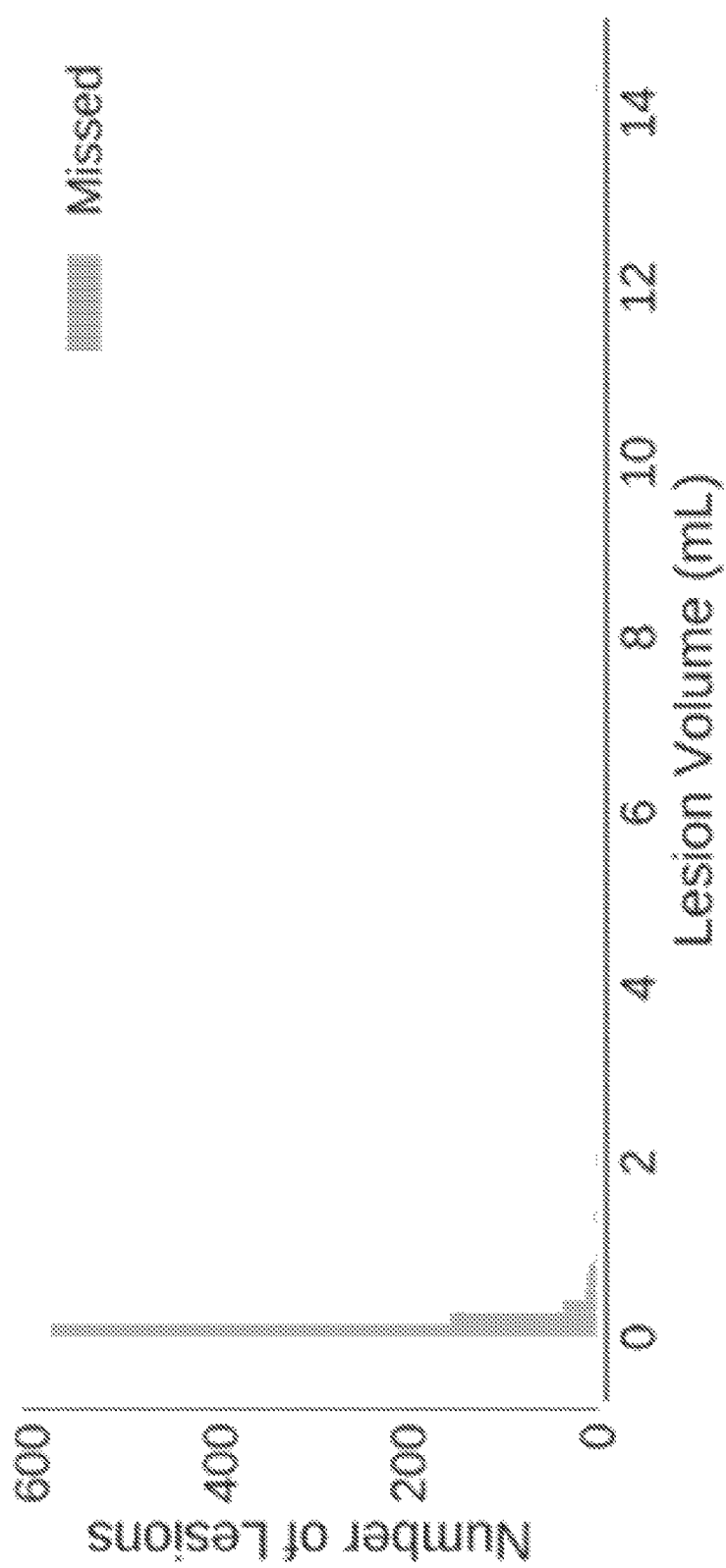
FIG. 6B is a histogram of missed lesions.
Figure 6C:
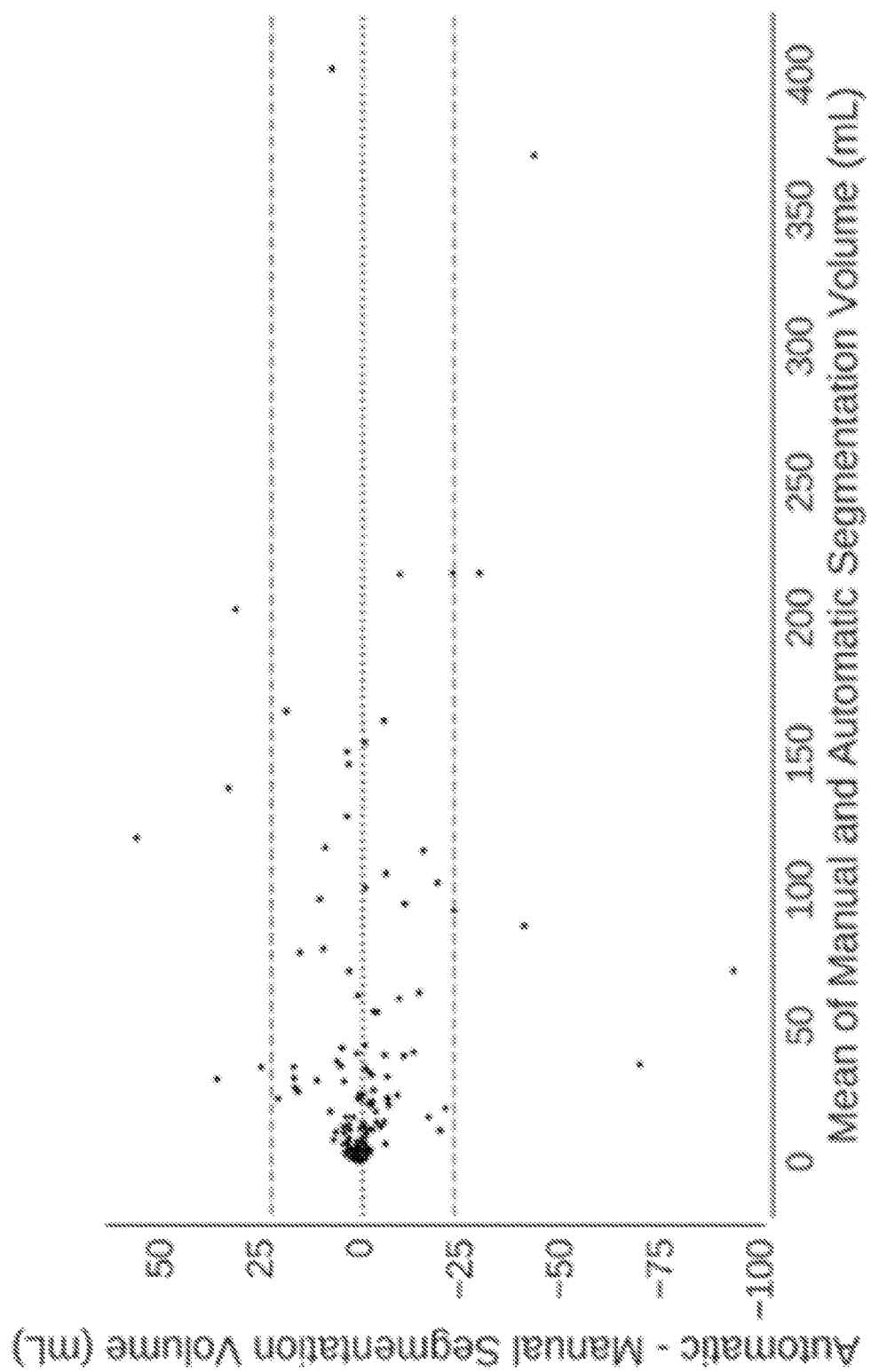
FIG. 6C is a Bland-Altman plot of automatic and manual lesion volumes on a per patient basis.

FIG. 6A shows a histogram of manual lesion volumes for detected lesions. FIG. 6B shows a histogram of missed lesions. FIG. 6C shows a Bland-Altman plot of automatic and manual lesion volumes on a per patient basis. The average volume of lesions detected was 9.085 mL while the average volume of lesions missed was 0.155 m. For patients with small infarcts (<median), the median dice coefficient was 0.657 (0.588-0.701). For patients with large infarct, the median dice coefficient was 0.816 (0.795-0.829).

Figure 7A:
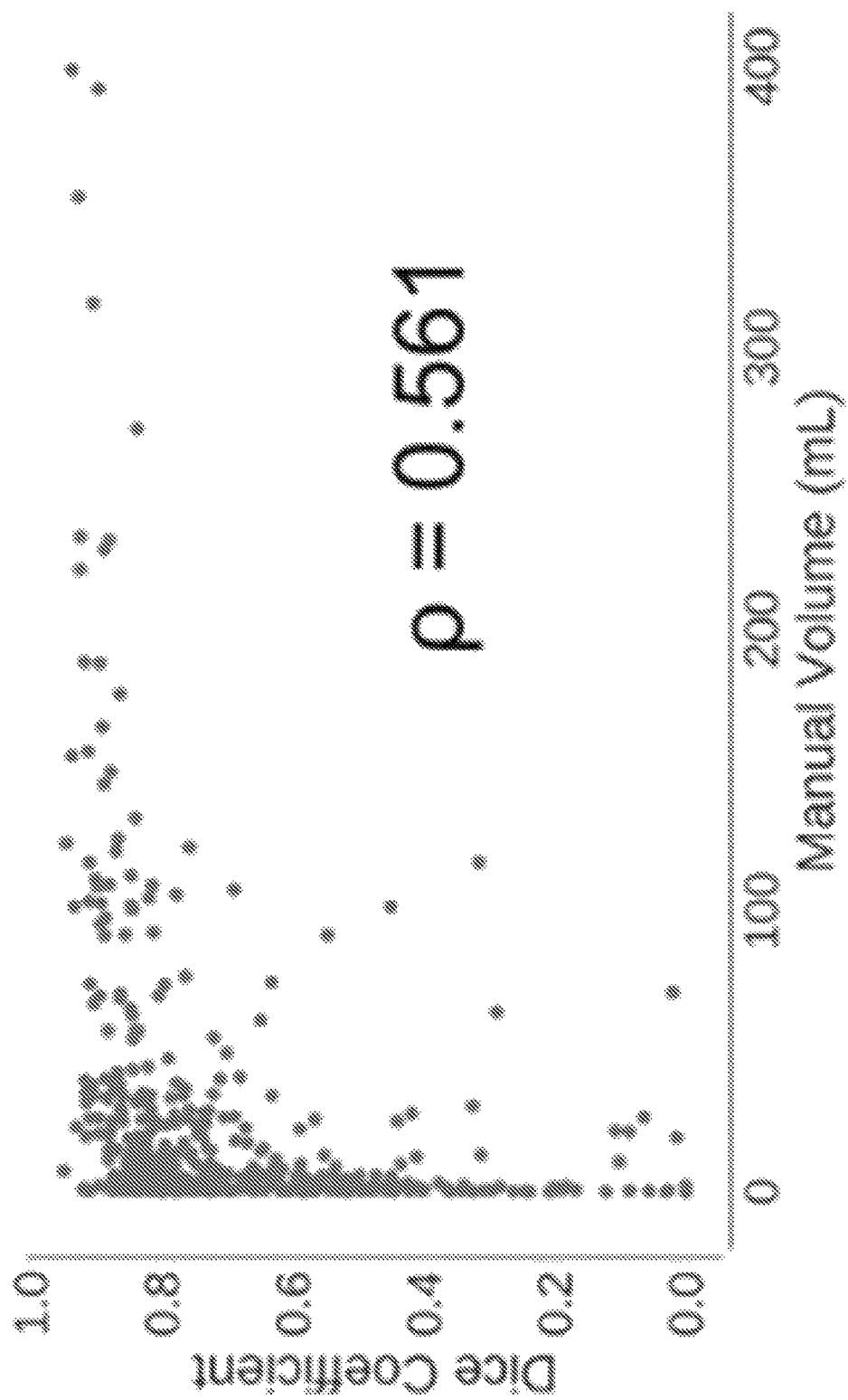
FIG. 7A is a scatter plot of dice coefficient vs manual volume.
Figure 7B:
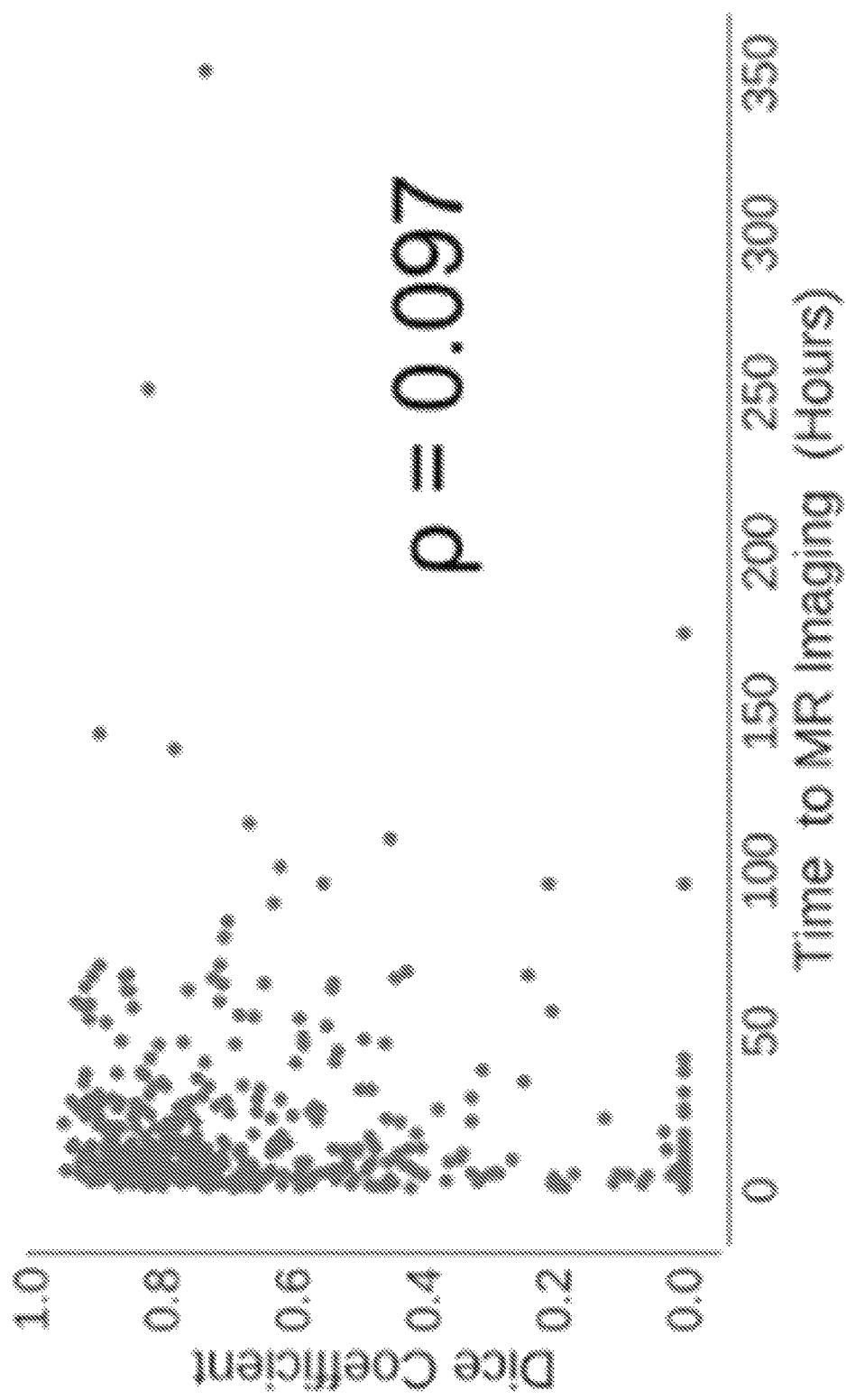
FIG. 7B is a scatter plot of dice coefficient vs time to MR imaging.
Figure 7C:
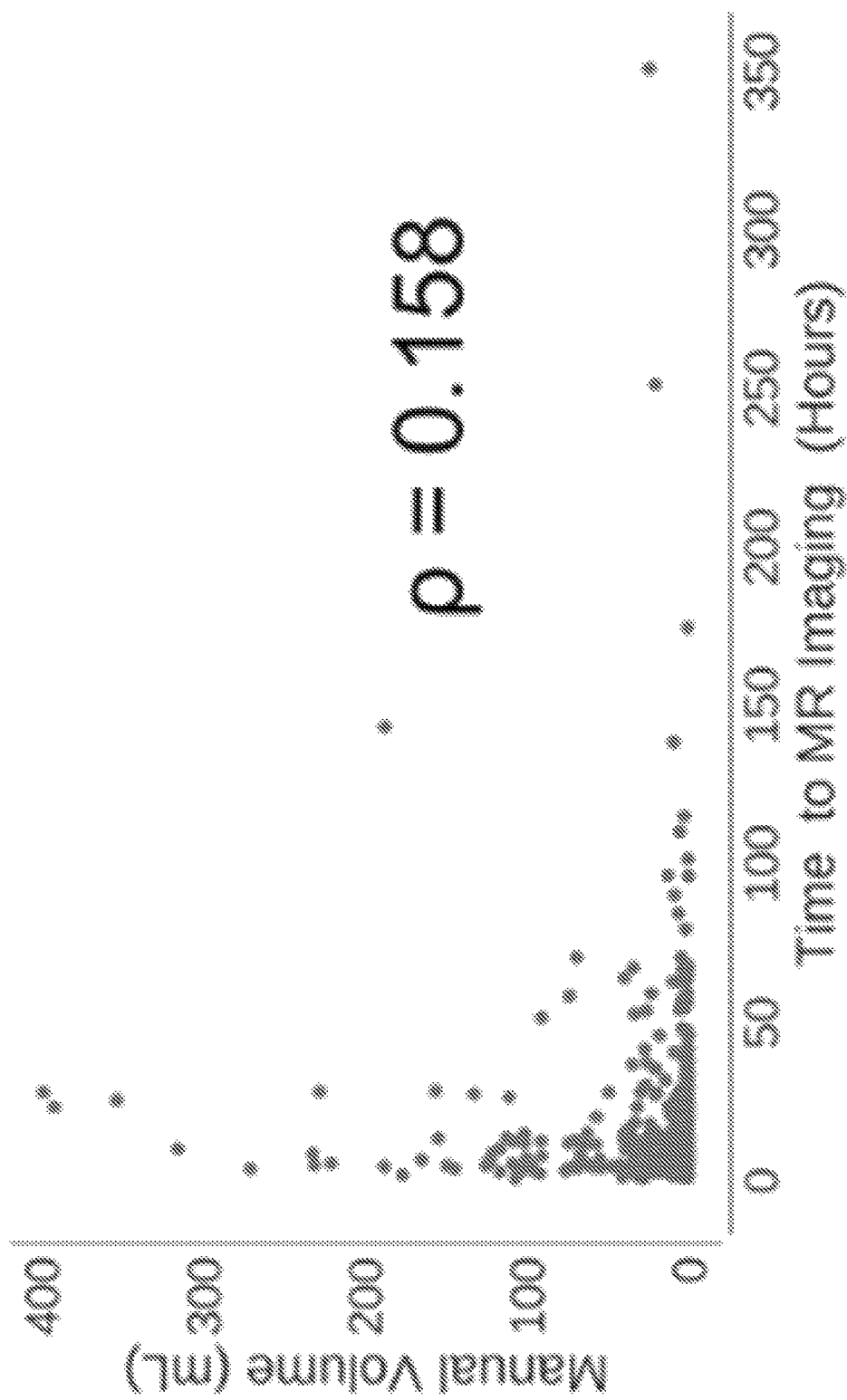
FIG. 7C is a scatter plot of manual volume vs time to MR imaging.

FIG. 7A shows a scatter plot of dice coefficient vs manual volume. FIG. 7B shows a scatter plot of dice coefficient vs time to MR imaging, FIG. 7C shows a scatter plot of manual volume vs time to MR imaging. There was a moderate association between dice coefficient and manual volume (Spearman's $p=0.561$, $p<0.001$). There was little association between dice coefficient and time to MR imaging ($p=0.097$) as well as manual volume and time to MR imaging ($p=0.158$).

Correlation Between Automated and Manual Volumes

Figure 8E:
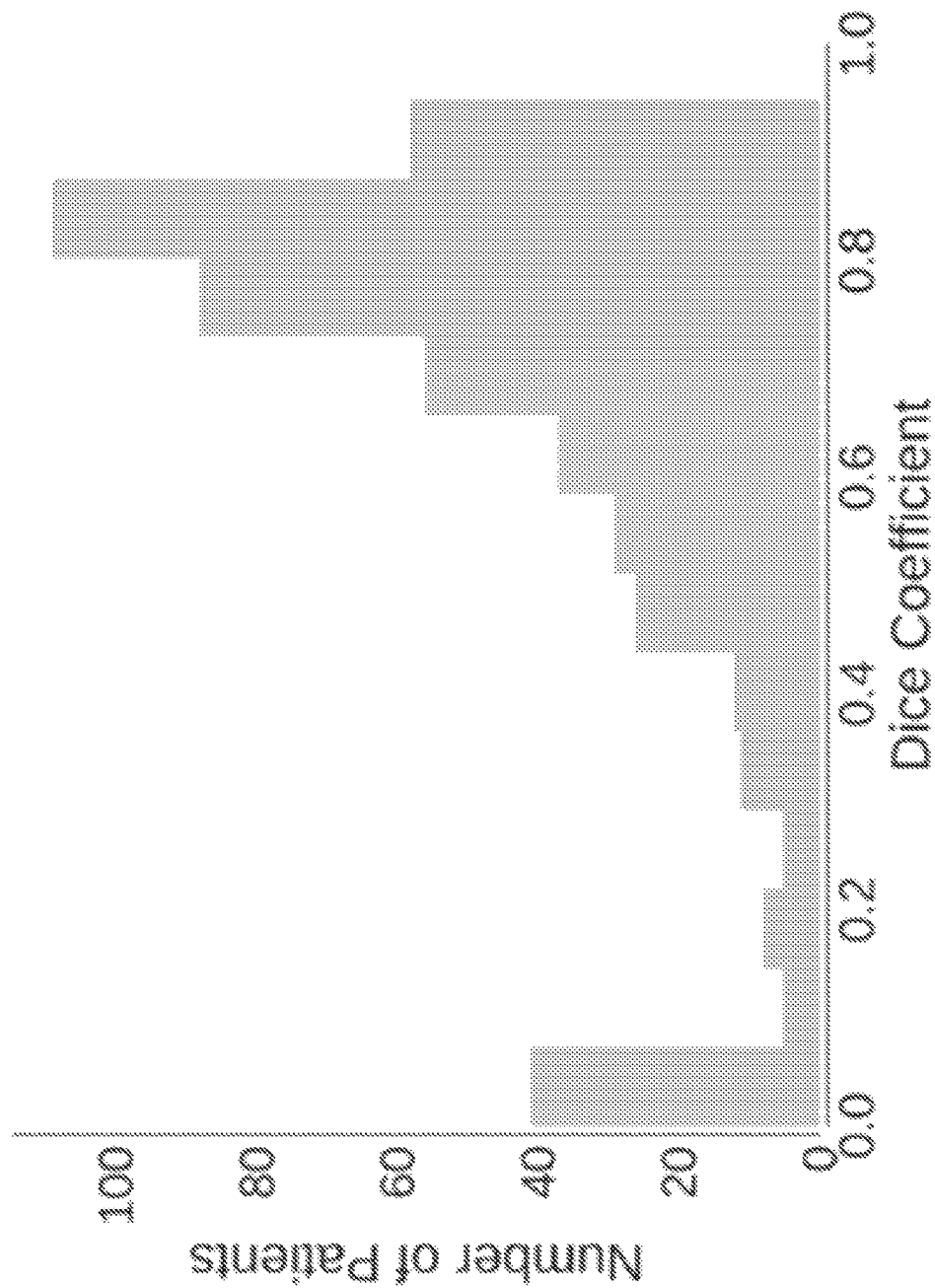
FIG. 8E is a histogram of dice similarity coefficients with the validation and testing sets for the ensemble of four Inception U-Nets.
Figure 8F:
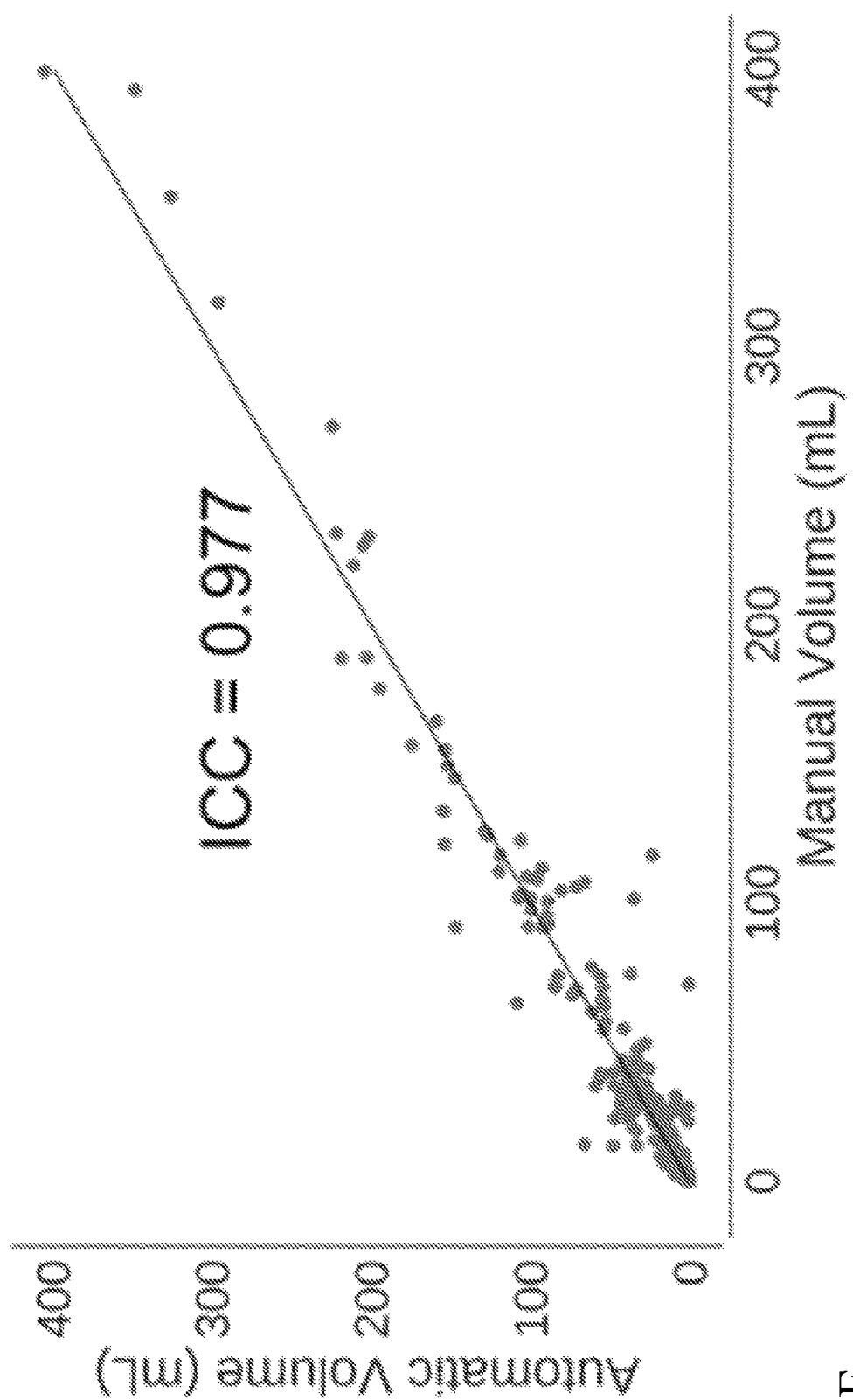
FIG. 8F is a scatter plot of manually vs automatically derived volumes with line of identity shown.

FIG. 8A shows an example of a manual segmentation on a first DWI image. FIG. 8B shows an example of a model generated segmentation on the first DWI image. FIG. 8C shows an example of a manual segmentation on a second DWI image. FIG. 8D shows an example of a model generated segmentation on the second DWI image. FIG. 8E shows a histogram of dice similarity coefficients with the validation and testing sets for the ensemble of four Inception U-Nets. FIG. 8F shows a scatter plot of manually vs automatically derived volumes with line of identity shown. In comparing manually and automatically derived infarct volumes (from ensemble of four Inception U-Nets), the intraclass correlation coefficient was 0.977 (p<0.0001) in the Validation and Testing Sets.

Qualitative Assessment by an Expert Stroke Neurologist

Table 5 below shows qualitative assessment of 47 manual and 47 automatic segmentations by an expert stroke neurologist (Expert 1), neuroradiologist (Expert 2), and radiologist (Expert 3). Question 1 asked whether the expert would edit the segmentation. Question 2 asked the expert to rate the quality of the segmentation on a scale of 1-4. Question 3 asked whether the expert believed the segmentation was performed by a human (as opposed to an algorithm). Results from question 1 and 3 are shown as percent of cases the expert stated yes. Results from question 2 are shown as the mean rating.

There were no statistically significant differences between manual and automatic segmentations for Questions 1-3 for Expert 1. For Expert 2, there were no statistically significant differences between manual and automatic segmentations for Question 2. However, Expert 2 would have edited 79% of the manual segmentations as opposed to 55% of the automatic segmentations (p<0.05). Additionally, Expert 2 believed 72% of the manual segmentations were performed by humans and 19% of the automatic segmentations were performed by humans (p<0.001). For Expert 3, there were no statistically significant differences between manual and automatic segmentations for Questions 1 and 3. However, Expert 3 rated automatic segmentations of higher quality than manual segmentations (p<0.05).

TABLE 5

| | | Ground Truth | | |
| --- | --- | --- | --- | --- |
| | | Manual (n = 47) | Algorithm (n = 47) | p-value |
| Expert 1 Neurologist | Question 1: Would edit? | 53% | 38% | 0.214 |
| | Question 2: Quality Rating? | 3.38 | 3.47 | 0.461 |
| | Question 3: Human annotator? | 57% | 55% | 1.000 |
| Expert 2 Neurologist | Question 1: Would edit? | 79% | 55% | 0.028 |
| | Question 2: Quality Rating? | 3.21 | 3.40 | 0.094 |
| | Question 3: Human annotator? | 72% | 19% | <0.001 |
| Expert 3 Neurologist | Question 1: Would edit? | 64% | 40% | 0.051 |
| | Question 2: Quality Rating? | 2.79 | 3.19 | 0.045 |
| | Question 3: Human annotator? | 72% | 62% | 0.374 |

Manual and Automatic Volume by 90-Day mRS Score

Figure 9A:
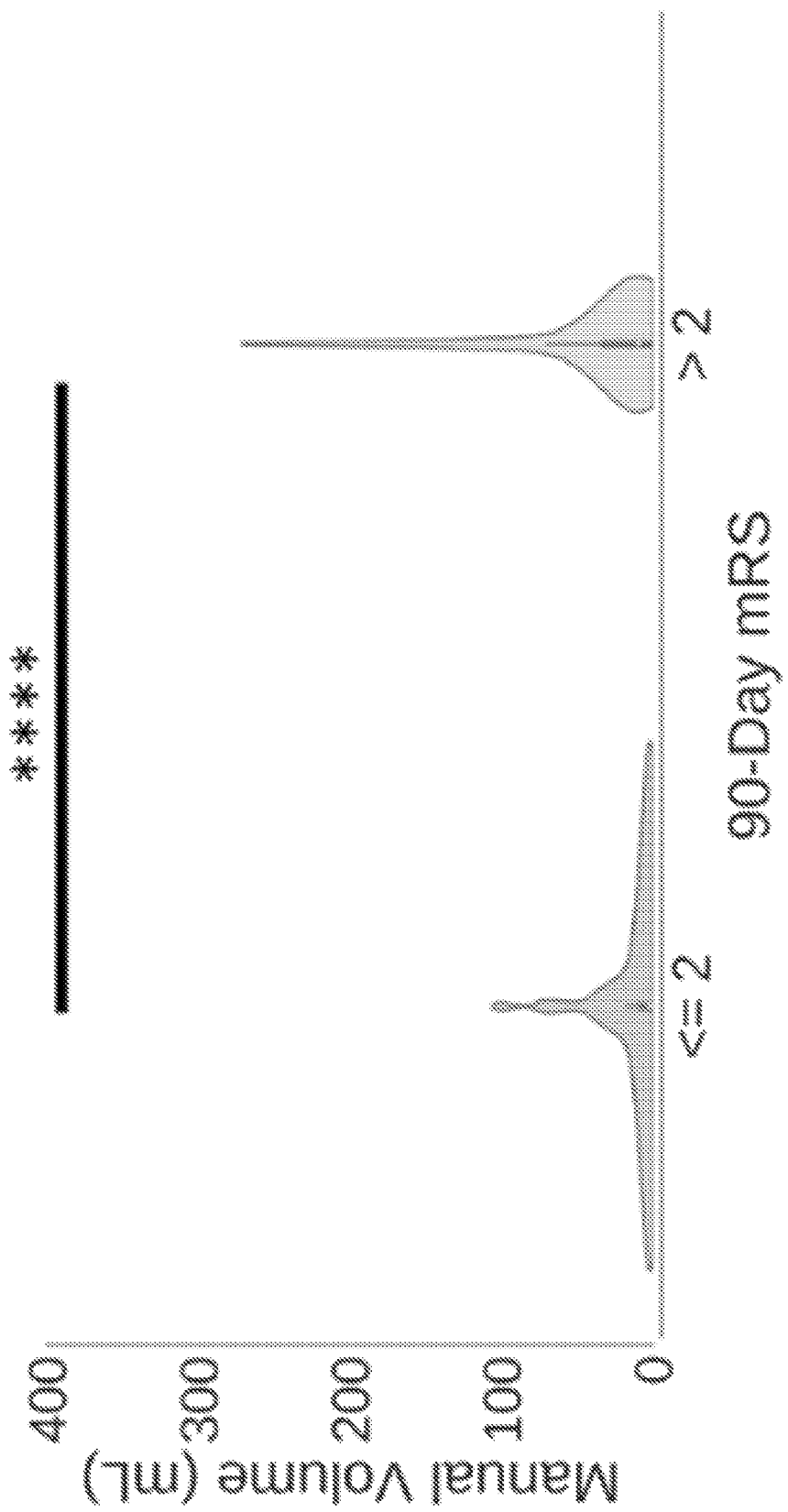
FIG. 9A is a violin plot of manually derived and automatically derived volumes from the ensemble of four inception U-Nets for patients with mRS<=2.
Figure 9B:
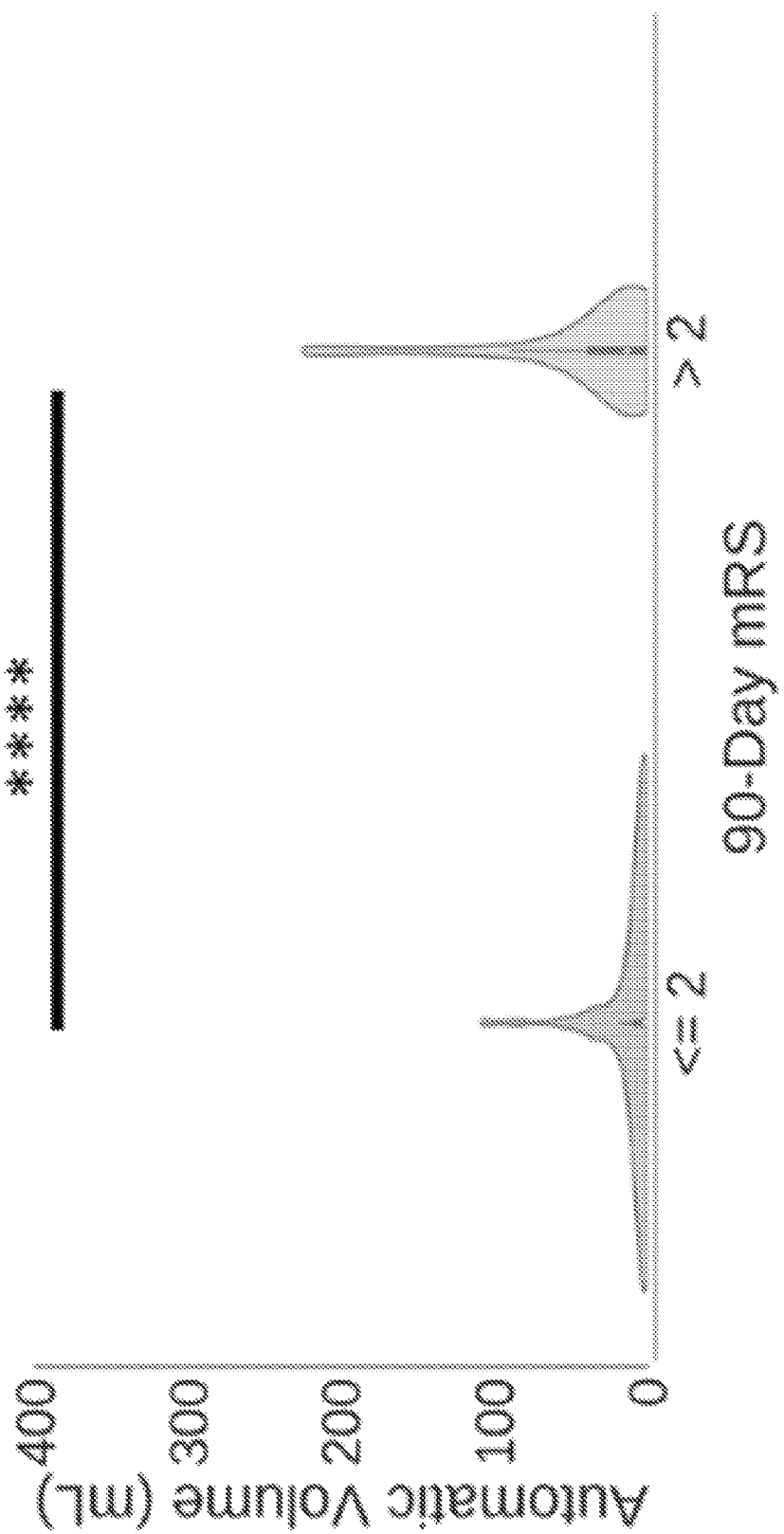
FIG. 9B is a violin plot of manually derived and automatically derived volumes from the ensemble of four inception U-Nets for patients with mRS>2.
Figure 9C:
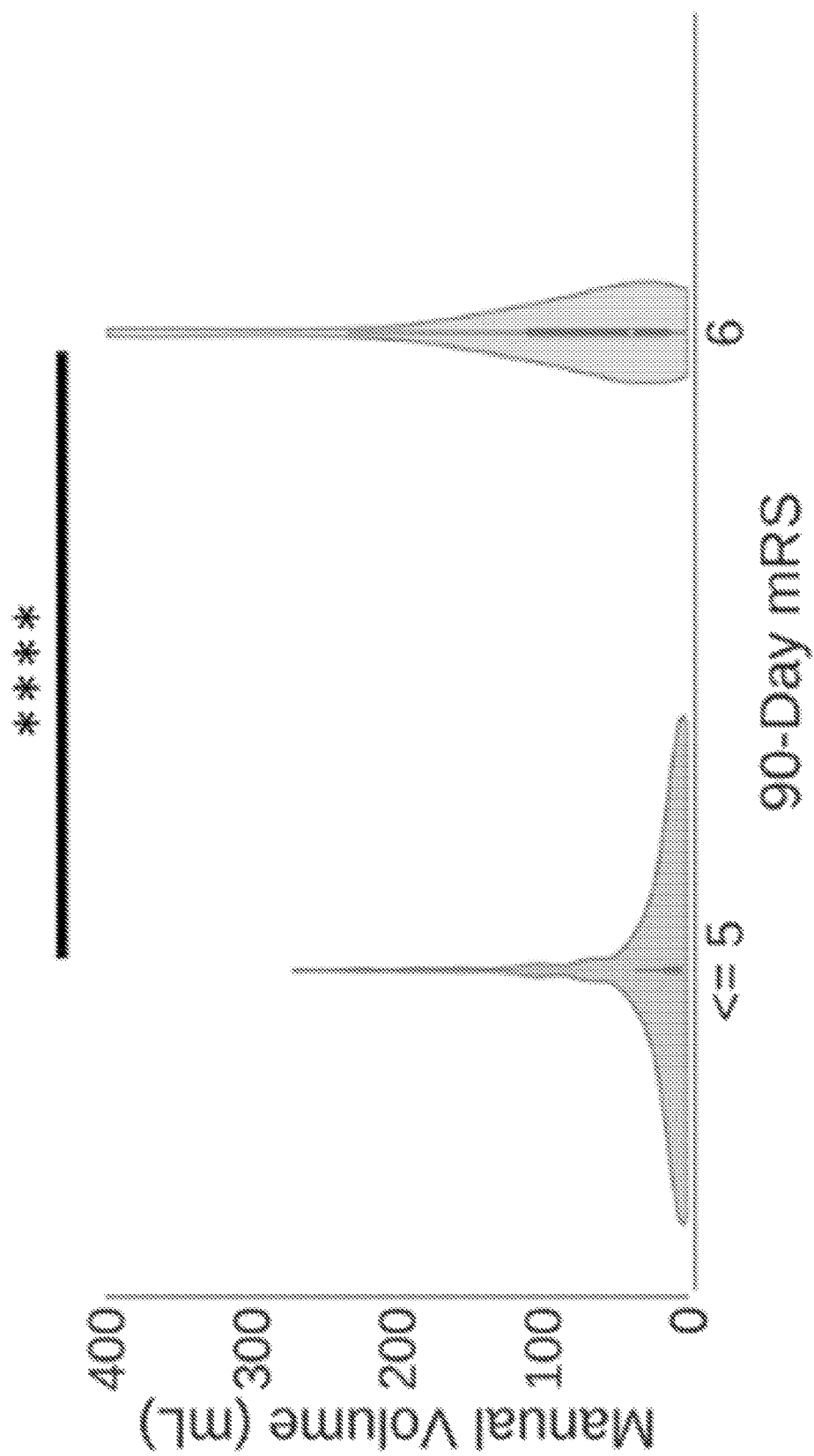
FIG. 9C is a violin plot of manually derived and automatically derived volumes from the ensemble of four inception U-Nets for patients with mRS<=5.
Figure 9D:
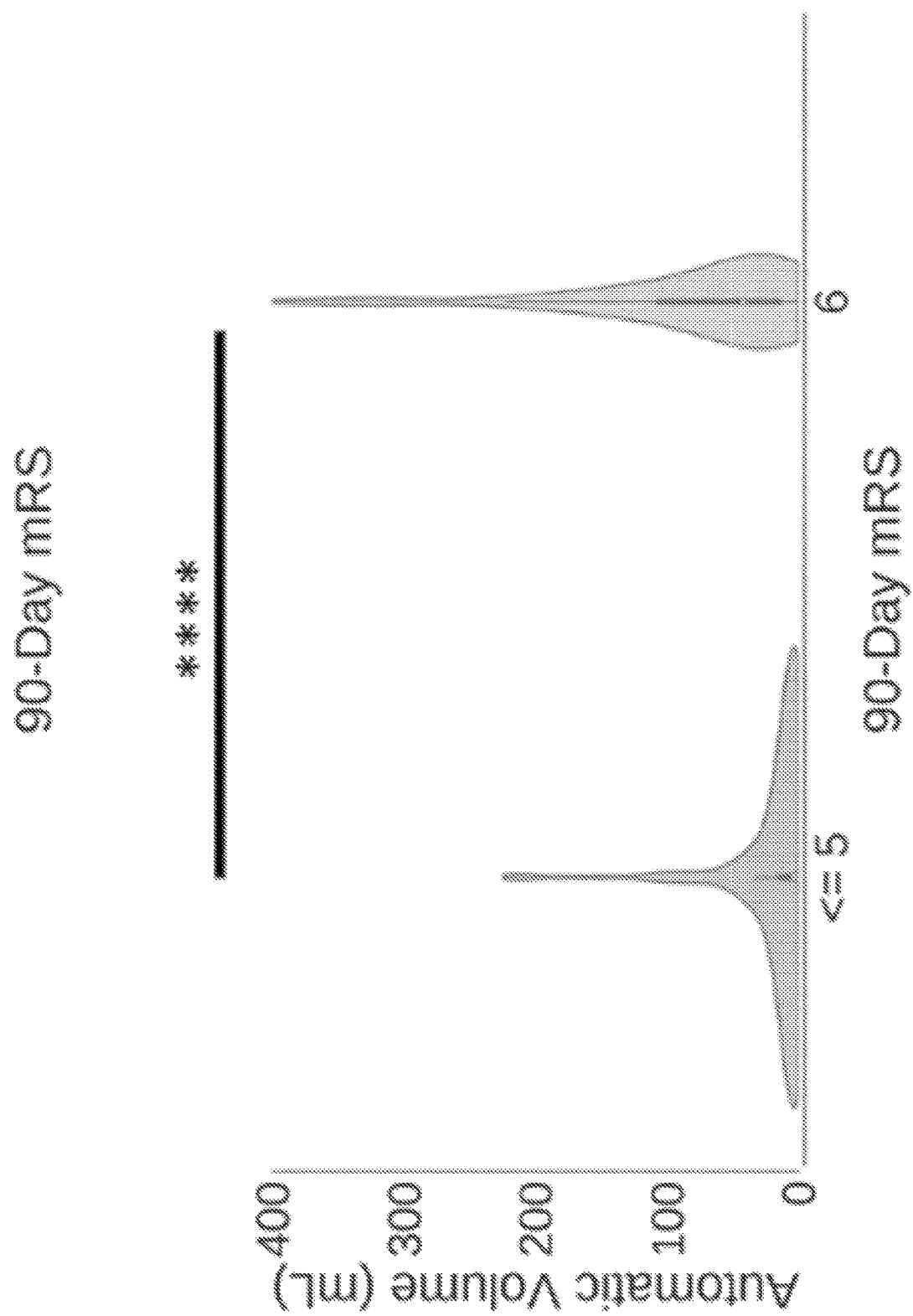
FIG. 9D is a violin plot of manually derived and automatically derived volumes from the ensemble of four inception U-Nets for patients with mRS>5.

FIG. 9A shows a violin plot of manually derived and automatically derived volumes from the ensemble of four inception U-Nets for patients with mRS<=2. FIG. 9B shows a violin plot of manually derived and automatically derived volumes from the ensemble of four inception U-Nets for patients with mRS>2. FIG. 9C shows a violin plot of manually derived and automatically derived volumes from the ensemble of four inception U-Nets for patients with mRS<=5. FIG. 9D shows a violin plot of manually derived and automatically derived volumes from the ensemble of four inception U-Nets for patients with mRS>5.

90-day mRS was missing for 71 patients and excluded from analysis of mRS. Patients were stratified based on mRS score at <=2 vs >2 (representing 90-day functional outcome) and at <=5 vs 6 (representing 90-day survival). Within the Validation and Testing Sets, the median manually derived volumes were 2.21 (1.87-2.75) mL, 9.79 (5.93-18.20) mL, 2.97 (2.43-3.69) mm3, and 38.79 (27.97-76.69) mL for patients with a 90-day mRS score of <=2, >2, <=5, and 6, respectively. The median of automatically derived volumes from the Ensemble of 4 Inception U-Nets was 1.96 (1.62-2.52) mL, 13.60 (5.25-18.82) mL, 2.86 (2.16-3.66) mL, and 41.44 (25.30-56.30) mL, respectively. For the manually derived volumes, there was a statistically significant difference between patients with mRS score<=2 vs. >2 (p<0.001) and mRS score<=5 vs. >5 (p<0.001). Similarly, for the automatically derived volumes, there was a statistically significant difference between patients with mRS score<=2 and >2 (p<0.001) and mRS score<=5 vs. >5 (p<0.001).

With minimal image pre-processing (e.g., no resampling and brain extraction), ensembling multiple Inception U-Nets resulted stroke detection rate, at 92.8% on the Validation and Testing Set. It was shown that there was no qualitative difference between manual and automatic segmentations via ratings from expert raters. All raters stated that they would edit a greater proportion of the manual segmentations compared to the automatic segmentations and one of the raters graded automatic segmentations as of significantly higher quality than manual segmentation.

In addition to segmentation accuracy, infarct volumes as derived from manual segmentations were also evaluated and our automatic deep learning segmentations, showing high agreement. Furthermore, statistical differences for non-disability vs disability and non-survivors vs survivors were present for both manually segmented and automatically segmented volumes. Thus, automatic volumetrics may serve as a useful tool to assist clinical decision-making as early identification of patients with expected poor outcomes may suggest alternative treatment and management strategies.

Infarct volume measurements are becoming an integral piece of stroke research. Continuous nature of the infarct volume data allows for exploring associations in smaller samples and making inferences with fewer data points as compared to categorical assessments based on visual inspection of neuroimaging. Also, categorical classifications massively suffer from high interrater disagreement. For instance, the interrater agreement to determine whether infarct size is less than or greater than one-third of the middle cerebral artery territory, which roughly corresponds to 100 ml, is only moderate (kappa=0.4). Infarct volume information is also frequently used by clinicians in practice for prediction of tissue and clinical outcome, assessment of the risk of developing hemorrhagic transformation or malignant edema, and assessment of eligibility for thrombolytic treatment or endovascular thrombectomy. Most clinical trials of intravenous and endovascular recanalization therapies have excluded patients who have already developed large infarcts because the risk of treatment complications such as symptomatic intracerebral hemorrhage outweighs the anticipated benefit in large infarcts. Infarcts exceeding one third of the middle cerebral artery territory are considered to be contraindication for intravenous thrombolysis. Similarly, most endovascular thrombectomy protocols exclude patients based on certain infarct volume thresholds that range from 20-70 ml depending on other associated clinical and imaging features of stroke. Conversely, some protocols attempt to avoid exposing patients with small infarcts to the risks, discomfort, and cost associated with recanalization treatments as such small infarcts causing minute structural brain injury confer a high recovery potential regardless of treatment. The major premise of the present study is that it provides a rapid and accurate means of obtaining infarct volume data; our automated algorithm provides infarct volumes within seconds. In contrast, manual outlining can take anywhere from a few minutes to half an hour depending on the lesion load and the experience level of the operator. Furthermore, in patients with multiple scattered infarcts, manual outlining takes even more time. The time required to manually outline a patient's infarcts may be around 10 to 15 minutes for expert neuroradiologists. The models described herein can generate lesion outlines rapidly and with minimal level of inconsistency and thus could be particularly useful in settings where there exists large quantities of data, such as in large consortia and multicenter repositories.

Thus, the present disclosure provides systems and methods for automatically analyzing image data.

The present invention has been described in terms of one or more preferred embodiments, and it should be appreciated that many equivalents, alternatives, variations, and modifications, aside from those expressly stated, are possible and within the scope of the invention.

The invention claimed is:

1. A image analysis system comprising at least one processor and at least one memory, the image analysis system configured to:
   receive image data associated with a brain of a patient, wherein the image data comprises a first three-dimensional (3D) diffusion weighted imaging (DWI) image acquired using a magnetic resonance imaging (MRI) system and a second 3D DWI image;
   concurrently provide the first 3D DWI image to a first channel of a trained model and the second 3D DWI image to a second channel of the trained model;
   receive an indicator associated with the first 3D DWI image and the second 3D DWI image from the model;
   generate a report based on the indicator; and
   cause the report to be output to at least one of a memory or a display.

2. The system of claim 1, wherein the first 3D DWI image is generated using a first b value, and the second 3D DWI image is generated using a second b value.

3. The system of claim 1, wherein the image data comprises a third 3D DWI image and a fourth 3D DWI image, at least a portion of the third 3D DWI image and the fourth 3D DWI image being associated with a different spatial location in the brain than at least a portion of the first 3D DWI image and the second 3D DWI, the system further configured to:
   provide the third 3D DWI image and the fourth 3D DWI image to the trained model;
   receive an indicator associated with the third 3D DWI image and the fourth 3D DWI image from the trained model; and
   generate the report further based on the indicator associated with the third 3D DWI image and the fourth 3D DWI image.

4. The system of claim 3, wherein a subset of pixels included in the third 3D DWI image and the fourth 3D DWI image and a subset of pixels included in the first 3D DWI image and the second 3D DWI image are associated with a common spatial area, and wherein the system is further configured to determine the presence of a lesion in the common spatial area based on the indicator associated with the third 3D DWI image and the fourth 3D DWI image and the indicator associated with the first 3D DWI image and the second 3D DWI image.

5. The system of claim 1, wherein the first 3D DWI image comprises a portion of a larger 3D DWI image of the brain of the patient.

6. The system of claim 1, wherein the first 3D DWI image is generated using a first set of imaging parameters, and the second 3D DWI image is generated using a second set of imaging parameters.

7. The system of claim 1, wherein the indicator includes a probability map indicative of locations in the brain of the patient where lesions have occurred.

8. The system of claim 1, wherein the model comprises a convolutional neural network comprising a number of inception modules.

9. The system of claim 8, wherein the model comprises a second convolutional neural network comprising a number of inception modules.

10. The system of claim 1, wherein the report comprises at least one of a segmentation map indicating locations of lesions in the brain of the patient or a volume of lesions in the brain of the patient.

11. The system of claim 1, wherein the report comprises a predicted occurrence of an ischemic stroke.

12. An image analysis method comprising:
   receiving image data associated with a brain of a patient, the image data comprising a first three-dimensional (3D) diffusion weighted image (DWI) image acquired using a magnetic resonance imaging (MRI) system and a second 3D DWI image;
   concurrently providing the first 3D DWI image to a first channel of a trained model and the second 3D DWI image to a second channel of the trained model;
   receiving an indicator associated with the first 3D DWI image and the second 3D DWI image from the model;
   generating a report based on the indicator; and
   causing the report to be output to at least one of a memory or a display.

13. The method of claim 12, wherein the first 3D DWI image is generated using a first b value, and the second 3D DWI image is generated using a second b value.

14. The method of claim 12, wherein the image data comprises a third 3D DWI image and a fourth 3D DWI image, at least a portion of the third 3D DWI image and the fourth 3D DWI image being associated with a different spatial location in the brain than at least a portion of the first 3D DWI image and the second 3D DWI, the method further comprising:
   providing the third 3D DWI image and the fourth 3D DWI image to the trained model;
   receiving an indicator associated with the third 3D DWI image and the fourth 3D DWI image from the trained model; and
   generating the report further based on the indicator associated with the third 3D DWI image and the fourth 3D DWI image.

15. The method of claim 14, wherein a subset of pixels included in the third 3D DWI image and the fourth 3D DWI image and a subset of pixels included in the first 3D DWI image and the second 3D DWI image are associated with a common spatial area, and wherein the method further comprises determining the presence of a lesion in the common spatial area based on the indicator associated with the third 3D DWI image and the fourth 3D DWI image and the indicator associated with the first 3D DWI image and the second 3D DWI image.

16. The method of claim 12, wherein the first 3D DWI image comprises a portion of a larger 3D DWI image of the brain of the patient.

17. The method of claim 12, wherein the first 3D DWI image is generated using a first set of imaging parameters, and the second 3D DWI image is generated using a second set of imaging parameters.

18. The method of claim 12, wherein the indicator includes a probability map indicative of locations in the brain of the patient where lesions have occurred.

19. The method of claim 12, wherein the model comprises a convolutional neural network comprising a number of inception modules.

20. The method of claim 19, wherein the model comprises a second convolutional neural network comprising a number of inception modules.

21. The method of claim 12, wherein the report comprises at least one of a segmentation map indicating locations of lesions in the brain of the patient or a volume of lesions in the brain of the patient.

22. The method of claim 12, wherein the report comprises a predicted occurrence of an ischemic stroke.

23. An ischemic stroke analysis system comprising at least one processor and at least one memory, the ischemic stroke analysis system configured to:
 receive image data associated with a brain of a patient, the image data comprising a first three-dimensional (3D) diffusion weighted imaging (DWI) image and a second 3D DWI image acquired using a magnetic resonance imaging (MRI) system;
 provide the image data to a trained model;
 receive an indicator associated with the first 3D DWI image and the second 3D DWI image from the model;
 generate a report comprising a segmentation map of lesions in the brain of the patient based on the indicator; and
 cause the report to be output to at least one of a memory or a display.

* * * * *